(12) United States Patent
Eliaz et al.

(10) Patent No.: US 7,964,183 B2
(45) Date of Patent: *Jun. 21, 2011

(54) COMPOSITION AND DOSAGE FORM COMPRISING A PARTICLE FORMULATION AND SUSPENDING VEHICLE

(75) Inventors: Rom Ezer Eliaz, Sunnyvale, CA (US); Yuanpeng Zhang, Cupertino, CA (US); Catherine Manya Rohloff, Cupertino, CA (US); Eric William Weeks, Oakland, CA (US); Gunjan Junnarkar, Palo Alto, CA (US)

(73) Assignee: Intarcia Therapeutics, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/655,397

(22) Filed: Dec. 29, 2009

(65) Prior Publication Data

US 2010/0112070 A1 May 6, 2010

Related U.S. Application Data

(63) Continuation of application No. 10/988,716, filed on Nov. 15, 2004, now Pat. No. 7,731,947.

(60) Provisional application No. 60/520,605, filed on Nov. 17, 2003.

(51) Int. Cl.
- *A61K 45/00* (2006.01)
- *A61K 38/26* (2006.01)
- *A61K 38/28* (2006.01)
- *A61K 38/18* (2006.01)
- *A61K 38/27* (2006.01)
- *A61F 13/00* (2006.01)
- *A61P 3/10* (2006.01)
- *A61P 5/06* (2006.01)
- *C07K 14/475* (2006.01)

(52) U.S. Cl. ......... 424/85.1; 424/422; 514/5.9; 514/7.2; 514/7.6; 514/11.4

(58) Field of Classification Search ................. 424/85.1, 424/422; 514/5.9, 7.2, 7.6, 11.4
See application file for complete search history.

(56) References Cited

U.S. PATENT DOCUMENTS

| | | |
|---|---|---|
| 4,111,201 A | 9/1978 | Theeuwes |
| 4,743,449 A | 5/1988 | Yoshida et al. |

(Continued)

FOREIGN PATENT DOCUMENTS

EP 0 729 747 B1 5/1997

(Continued)

OTHER PUBLICATIONS

Bakan, D. et al., "Physicochemical Characterization of a Synthetic Lipid Emulsion for Hepatocyte-Selective Delivery of Lipophilic Compounds: Application to Polyiodinated triglycerides as Contrast Agents for Compound Tomography", *Journal of Pharmaceutical Science*, 1996, 85(9), 908-914.

(Continued)

*Primary Examiner* — San-Ming Hui
*Assistant Examiner* — Paul Zarek
(74) *Attorney, Agent, or Firm* — Gary R. Fabian; Barbara G. McClung

(57) ABSTRACT

A liquid composition in an osmotic drug delivery system and a dosage form in an osmotic drug delivery system is disclosed comprising an amphiphilic molecule, a non-aqueous liquid solvent, and a pharmaceutically active agent.

22 Claims, 14 Drawing Sheets

U.S. PATENT DOCUMENTS

| | | |
|---|---|---|
| 5,091,188 A | 2/1992 | Haynes |
| 5,278,151 A | 1/1994 | Korb et al. |
| 5,324,280 A | 6/1994 | Wong et al. |
| 5,660,858 A | 8/1997 | Parikh et al. |
| 5,728,396 A | 3/1998 | Peery et al. |
| 5,904,935 A | 5/1999 | Eckenhoff et al. |
| 5,932,547 A | 8/1999 | Stevenson et al. |
| 5,972,370 A | 10/1999 | Eckenhoff et al. |
| 5,997,527 A | 12/1999 | Gumucio et al. |
| 6,022,561 A | 2/2000 | Carlsson et al. |
| 6,113,938 A | 9/2000 | Chen et al. |
| 6,124,261 A | 9/2000 | Stevenson et al. |
| 6,130,200 A | 10/2000 | Brodbeck et al. |
| 6,132,420 A | 10/2000 | Dionne et al. |
| 6,133,249 A | 10/2000 | Hills |
| 6,174,547 B1 | 1/2001 | Dong et al. |
| 6,235,712 B1 | 5/2001 | Stevenson et al. |
| 6,258,377 B1 | 7/2001 | New et al. |
| 6,270,787 B1 | 8/2001 | Ayer |
| 6,287,295 B1 | 9/2001 | Chen et al. |
| 6,331,311 B1 | 12/2001 | Brodbeck et al. |
| 6,375,978 B1 | 4/2002 | Kleiner et al. |
| 6,419,952 B2 | 7/2002 | Wong et al. |
| 6,433,144 B1 | 8/2002 | Morris et al. |
| 6,461,605 B1 | 10/2002 | Cutler et al. |
| 6,468,961 B1 | 10/2002 | Brodbeck et al. |
| 6,485,706 B1 | 11/2002 | McCoy et al. |
| 6,508,808 B1 | 1/2003 | Carr et al. |
| 6,524,305 B1 | 2/2003 | Peterson et al. |
| 6,544,252 B1 | 4/2003 | Theeuwes et al. |
| 6,551,613 B1 | 4/2003 | Dong et al. |
| 6,673,767 B1 | 1/2004 | Brodbeck et al. |
| 6,939,556 B2 | 9/2005 | Lautenbach |
| 7,014,636 B2 | 3/2006 | Gilbert |
| 7,074,423 B2 | 7/2006 | Fereira et al. |
| 7,163,688 B2 | 1/2007 | Peery et al. |
| 7,207,982 B2 | 4/2007 | Dionne et al. |
| 7,258,869 B1 | 8/2007 | Berry et al. |
| 7,731,947 B2 * | 6/2010 | Eliaz et al. .................. 424/85.4 |
| 2003/0059376 A1 | 3/2003 | Libbey, III et al. |
| 2004/0224903 A1 | 11/2004 | Berry et al. |
| 2005/0008661 A1 | 1/2005 | Fereira et al. |
| 2005/0112188 A1 | 5/2005 | Eliaz et al. |
| 2005/0175701 A1 | 8/2005 | Pan et al. |
| 2005/0266087 A1 | 12/2005 | Junnarkar et al. |
| 2005/0276856 A1 | 12/2005 | Fereira et al. |
| 2006/0193918 A1 | 8/2006 | Rohloff et al. |
| 2006/0216242 A1 | 9/2006 | Rohloff et al. |
| 2006/0246138 A1 | 11/2006 | Rohloff et al. |
| 2006/0251618 A1 | 11/2006 | Dennis et al. |
| 2007/0027105 A1 | 2/2007 | Junnarkar et al. |
| 2007/0281024 A1 | 12/2007 | Lautenbach et al. |

FOREIGN PATENT DOCUMENTS

| | | |
|---|---|---|
| EP | 0 771 817 A2 | 5/1997 |
| JP | 9-241153 | 9/1997 |
| JP | 11-100353 | 4/1999 |
| WO | WO 93/06819 | 4/1993 |
| WO | WO 97/15289 | 5/1997 |
| WO | WO 97/46204 | 12/1997 |
| WO | WO 98/32463 | 7/1998 |
| WO | WO 98/47487 | 10/1998 |
| WO | WO 99/16419 | 4/1999 |
| WO | WO 99/39700 | 8/1999 |
| WO | WO 00/45790 | 8/2000 |
| WO | WO 00/67728 | 11/2000 |
| WO | WO 02/45752 | 6/2002 |
| WO | WO 02/069983 | 9/2002 |
| WO | WO 03/053400 | 7/2003 |

OTHER PUBLICATIONS

Cantor, R.S., "Theory of Lipid Monolayers Comprised of Mixtures of Flexible and Stiff Amphiphiles in Anthermal Solvents: Fluid Phase Coexistence", *The Journal of Chemical Physics*, 1996, 104(20), 8082-8095.

Chapman, D. et al., "Physical Studies of Phospholipids. VI. Thermotropic and Lyotropic Mesomorphism of Some 1,2-Diacylphosphatidylcholines (lecithins)", *Chemistry and Physics of Lipids*, 1967, 1(5), 445-475.

Felker, T.E. et al., "The Rate of Transfer of Unesterified Cholesterol from Rat Erythrocytes to Emulsions Modeling Nascent *Triglyceride*-Rich Lipoproteins and Chylomicrons Depends on the Degree of Fluidity of the Surface", *The Journal of Nutritional Biochemistry*, 1993, 4(1), 630-634.

Kabalnov, A. et al., "Phospholipids as Emulsion Stabilizers.2. Phase Behavior Versus Emulsion Stability", *Journal of Colloid and Interface Science*, 1996, 184(1), 227-235.

Kabalnov, A. et al., "Macroemulsion Type and Stability of Alkane-Water-Phospholipid Systems", *Book of Abstracts, $210^{th}$ ACS National Meeting*, Chicago, Il, Aug. 20-24, 1995, Issue Pt 1.

Massey, John B., "Interaction of Vitamin E with Saturated Phospholipid Bilayers", *Biochemical and Biophysical Research Communications*, 1982, 106(3), 842-847.

Wang, X. et al., "Preferential Interaction of α-tocopherol with Phosphatidylcholines in Mixed Aqueous Dispersions of Phosphatidylcholine and Phosphatidylethanolamine", *European Journal of Biochemistry*, 2000, 267(21), 6362-6368.

Wang, X. et al., "Ripple Phases Induced by α-Tocopherol in Saturated Diacylphosphatidylcholines", *Archives of Biochemistry and Biophysics*, 2000, 377(2), 304-314.

Wang, X.Y. et al., "The Distribution of α-Tocopherol in Mixed Aqueous Dispersions of Phosphatidyleholine and Phosphatidylethanolamine", *Biochimica et Biophysica Acta-Biomembranes*, 2000, 1509(1-2), 361-372.

Jain, R.A. et al., "Controlled Delivery of Drugs from a Novel Injectable in Situ Formed Biodegradable PLGA Microsphere System", *Journal of Microencapsulation*, 2000, 17(3), 343-362.

Fujii, M. et al., "Effect of *phosphatidylcholine* on Skin Permeation of Indomethacin from gel prepared with Liquid Paraffin and Hydrogenated Phospholipid", *International Journal of Pharmaceutics*, 2001, 222(1), 57-64.

Fujii, M. et al., Enhancement of Skin Permeation of Miconazole by Phospholipid and Dodecyl 2-(N, N-dimethylamino) Propionate (DDAIP), *International Journal of Pharmaceutics*, 2002, 234(1-2), 121-128.

Schmalfuβ, U. et al., "Modification of Drug Penetration into Human Skin Using Microemulsions", *Journal of Controlled Release*, 1997, 46(3), 279-285.

Erös, I. et al., "Multiple Phase Emulsions as Controlled Drug Delivery Therapeutic Systems", *Proc.-Conf. Colloid Chem.*, 1993, $6^{th}$ Meeting Date, 193-196.

Nordén, T.P. et al., "Physicochemical Characterization of a Drug-Containing Phospholipid-Stabilized o/w Emulsion for Intravenous Administration", *European Journal of Pharmaceutical Sciences*, 2001, 13(4), 393-401.

Bakhtiar, C. et al, Taking Delivery. (Ingredients: Liposomes). (liposomes in cosmetic delivery systems), *Soap Perfumery & Cosmetics*, 2003, 76(3), 59(4).

Das, S. et al., "Reviewing Antisense Oligonucleotide Therapy: Part 2, Delivery Issues", *BioPharm*, Nov. 1999, 12(11), 44.

Larsson, K., "Stability of Emulsions Formed by Polar Lipids", *Progress in the Chemistry of Fats and Other Lipids*, 1978, 16, 163-169.

Ortiz, A. et al., A Differential Scanning Calorimetry Study of the Interaction of α-*Tocopherol* with Mixtures of Phospholipids, *Biochim et Biophys Acta*, 1987, 898(2), 214-222.

Lundberg, B.., "A Submicron Lipid Emulsion Coated with Amphipathic Polyethylene Glycol for Parenteral Administration of Paclitaxel (Taxol)", *The Journal of Pharmacy and Pharmacology*, 1997, 49(1), 16-21.

Hodoshima, N. et al., "Lipid Nanoparticles for Delivering Antitumor Drugs", *International Journal of Pharmaceutics*, 1997, 146(1), 81-92.

Quintanar Guerrero D. et al., "Applications of the Ion-Pair Concept to Hydrophilic Substances with Special Emphasis on Peptides", *Pharmaceutical Research*, 1997, 14(2), 119-127.

Bauer, K.H. et al., "Non Aqueous Emulsions as Vehicles for Capsule Fillings", *Drug Development and Industrial Pharmacy*, 1984, 10(5), 699-712.

Bohlinder, K. et al., "Use and Characteristics of a Novel Lipid Particle-Forming Matrix as a *Drug*-Carrier System", *European Journal of Pharmaceutical Sciences*, 1994, 2(4), 271-279.

Supplementary European Search Report, Application No. EP 04 81 1199, Jun. 2, 2009 (EP Application No. 04 81 1199 is a foreign application related to the present U.S. application).

Chaumeil, J.C., "Micronization: A Method of Improving the Bioavailability of Poorly Soluble Drugs, "Methods and Findings in Experimental and Clinical Pharmacology, Apr. 1998, 20(3), 211-215.

* cited by examiner

Figure 12

COMPOSITION AND DOSAGE FORM COMPRISING A PARTICLE FORMULATION AND SUSPENDING VEHICLE

CROSS-REFERENCE TO RELATED APPLICATIONS

This application is a continuation of U.S. patent application Ser. No. 10/988,716, filed on 15 Nov. 2004, now U.S. Pat. No. 7,731,947 which claims the benefit of U.S. Provisional Application Ser. No. 60/520,605, filed on 17 Nov. 2003, now expired, which applications are incorporated herein by reference in their entireties.

FIELD

The present invention relates to liquid composition in an osmotic drug delivery system and a dosage form of a liquid composition in an osmotic drug delivery device.

BACKGROUND

Development of drug suspension formulations designed for delivery from sustained delivery devices and osmotic delivery devices has resulted in a family of compositions utilizing polymer or surfactant solutions, non-aqueous liquid solvents or blends of solvents for polymer. The polymer acts as a viscosity modifier to provide acceptable stability of the suspension during self storage and performance intervals. These polymer solutions provide a stable environment for pharmaceutically active agents, e.g., small molecule drugs or therapeutic proteins or peptides.

Drug delivery devices attempt to deliver low solubility drugs by incorporating liquid drug formulations that are released at a controlled rate over time. These osmotic delivery devices are disclosed in U.S. Pat. Nos. 4,111,201; 5,324,280; 5,413,672; and 6,174,547. However, such liquid osmotic delivery systems are limited in the concentration of drug in the liquid formulation and hence, the drug loading available, leading to delivery systems that can be of an unacceptably large size, volume, or number for therapeutic purposes.

Polymers, such as polyvinyl pyrrolidone (PVP), exhibit solubility in a wide range of non-aqueous liquid solvents, but PVP is also quite soluble in water. As a result, highly viscous PVP/water gels can be produced near the formulation/water interface. These viscous gels can occlude the delivery conduit of the drug delivery device, interfering with performance of the delivery device. A need exists in the art to develop a viscous liquid compositions with improved performance characteristics in drug delivery devices, for example, osmotic drug delivery devices. There also exists a need to eliminate pluggage of discharge ports of implantable devices. Additionally, there is a need for suspending vehicles that are substantially resistant to phase separation while at the same time are sufficiently viscous to suspend pharmaceutical agents for long periods of time. Further, it is desirable to formulate polymer-free dosage forms which remain substantially homogenous for a desired dosaging time.

SUMMARY

The invention is generally related to drug delivery compositions comprising amphiphilic molecules in combination with a solvent form liquid compositions with desired properties that exhibit a desired viscosity and that exhibit a desired solvency in water. The viscous liquid compositions are useful for therapeutic drug delivery applications in which the formulation can be slowly introduced into an aqueous environment.

In one embodiment, a liquid composition in an osmotic drug delivery system comprises an amphiphilic molecule, a non-aqueous liquid solvent, and a pharmaceutically active agent. In a further embodiment, amphiphilic molecules include, but are not limited to, lipids, surfactants, amphiphilic block polymers, or amphiphilic proteins or peptides. In a further detailed embodiment, the lipid is selected from saturated lipid, unsaturated lipid, neutral lipid, anionic lipid, cationic lipid, natural lipid or synthetic lipid.

Amphiphilic molecules, for example, lipids, in combination with a solvent, form a viscous liquid formulation that exhibits a desired solvency in water for drug delivery applications in which the formulation is slowly introduced into an aqueous environment. Amphiphilic molecules, such as lipids, in non-aqueous liquid solvents can provide viscous liquid compositions for therapeutic drug or protein delivery in a system or delivery device that avoids problems of precipitation, aggregation, or formation of highly viscous gels at the lipid/solvent/water interface. The liquid composition overcomes problems which can limit delivery of a therapeutic composition from the delivery device. Amphiphilic molecules, such as lipids, in non-aqueous liquid solvents deliver therapeutic drugs or proteins from a delivery device into an aqueous environment in a continuous measured flow to the target tissue of interest.

Amphiphilic molecules, e.g., lipids in non-aqueous liquid solvents, can replace delivery systems comprising high molecular weight molecules, e.g., polymers such as PVP or PLGA, when forming therapeutic drug delivery systems in which particular rheological properties are desired. When introduced into an aqueous environment, lipids can be amphiphilic molecules capable of forming small self-assembled structures in water with forms ranging from bi-layers (multilamellar vesicles, unilamellar vesicles/liposomes) to micelles and even inverted micelles (hexagonal structure).

Drug delivery compositions comprising lipids in non-aqueous liquid solvents have been formulated into stable suspensions of a therapeutic drug suitable for dispensing from osmotic delivery devices for extended intervals. Compositions comprising lipids and non-aqueous liquid solvents can exhibit a variety of solubility properties in water and further can exhibit significant partitioning of the lipids at a water interface resulting in viscous liquid compositions e.g., viscous lipid gels.

In a further embodiment, drug delivery compositions comprising lipids in non-aqueous liquid solvents have been formulated into stable suspensions wherein the pharmaceutically active agent is suspended in a particle within said liquid composition. The particles containing the pharmaceutically active agent can be formed by a number of different processes, e.g., spray drying, lyophilization, or supercritical fluid processing.

In a detailed embodiment, non-aqueous liquid solvents useful to produce such gels include, but are not limited to, lauryl lactate (LL), lauryl alcohol (LA), benzyl alcohol (BA), benzyl benzoate (BB), 1:1 benzyl benzoate:benzyl alcohol, benzyl alcohol, ethyl hexyl lactate, glycerol formal, tetraglycol (glycofurol; GF), N-1-methyl-2-pyrrolidone (NMP), dimethyl sulfoxide, (DMSO), polyethyleneglycol (e.g., PEG 400), triglycerides (triolein, trilaurin, tricarprin, tricaprylin), ethanol, isopropanol, t-butyl alcohol, cyclohexanol, glycerin, glycerol, α-tocopherol (vitamin E) vegetable oil, sesame oil, soybean oil, cottonseed oil or peanut oil.

Various amphiphilic molecules can be used, e.g., lipids, surfactants, amphiphilic block polymers, or amphiphilic proteins or peptides. Lipid molecules include, but are not limited to, saturated and unsaturated lipids; neutral, cationic, or anionic lipids; or natural or synthetic lipids. Anionic lipids can induce formation of a helical segment of a protein, and can play an important physiological role. In a detailed embodiment, lipids can be one or a mixture of two or more from any of the following classes including, but not limited to: phosphatidylcholine (PC), phosphatidylethanolamine (PE), phosphatidylglycerol (PG), phosphosphatidylinositol (PI), phosphatidylserine (PS), phosphatidic acid (PA) sphingomyelin (SM).

In a detailed embodiment, individual lipids include, but are not limited to: neutral lipids—dioleoyl phosphatidylcholine (DOPC), dimyristoylphosphatidylcholine (DMPC), dipalmitoylphosphatidylcholine (DPPC), distearoylphosphatidylcholine (DSPC), egg phosphatidylcholine (egg PC), soy phosphatidylcholine (soy PC), partially or fully hydrogenated phosphatidylcholines (PHSPC or HSPC), palmitoyl-oleoyl phosphatidylcholine (POPC), stearyloleoylphosphatidylcholine (SOPC); and anionic lipids—dioleoy phosphatidylglycerol (DOPG), dimyristoylphosphatidylglycerol (DMPG), dipalmitoylphosphatidylglyserol (DPPG), distearoylphosphatidylglyserol (DSPG). Various PEG (polyethylene glycol)-lipids can also be included for added benefit. Examples of PEG-lipids include, but are not limited to mPEG-DPPE, mPEG-DMPE, mPEG-DSPE, -mPEG-ceramide-DSPE, or mPEG-DS. Block copolymer surfactants (e.g., Pluronic® surfactants or Pluronic® surfactant F-127), or sorbitan esters structurants (e.g., Span® 80, Sigma Aldrich Chemical Co.) can be used. Moreover, when needed, increments of anti-oxidant lipid agents including, but not limited to, vitamin E, α-tocopherol, or ascorbic acid, can be added to prevent oxidation or peroxide formation. The increments of anti-oxidant lipid agents are already a part of the PHSPC formulations.

Amphiphilic molecule weight percent in the formulation can range from about 1 to about 100 weight percent, in detailed embodiments. Solvent weight percent in the formulation can range from about 0 to about 99 weight percent.

In a further embodiment, the pharmaceutically active agent is selected from a protein, peptide, small molecule drug, lipid drug or nucleic acid drug (e.g., DNA, RNA, antisense, ribozyme, DNAzyme, and the like).

The liquid composition is a viscous liquid composition, in a further detailed embodiment. The viscosity of the composition can be from about 1 to about 100,000 poise. A ratio by weight of amphiphilic molecule to non-aqueous liquid solvent can be between about 1 and about 4.

In a further embodiment, the pharmaceutically active agent is selected from biologically or pharmacologically active substance. In a detailed embodiment, the pharmaceutically active agent is ω-interferon, α-interferon, β-interferon, γ-interferon, erythropoietin, human growth hormone, granulocyte macrophage colony stimulating factor (GM-CSF), human growth hormone releasing hormone (huGHRH), insulin, desmopressin, infliximab, antibody or an agent conjugated to a targeting ligand, risperidone, paliperidone, glucagon-like peptide-1 (GLP-1), or bone morphogenic protein. The pharmaceutically active agent can be combined with sucrose, methionine and citrate in weight ratios of 1 to 2 to 1 to 2.15.

In another embodiment, a dosage form for osmotic drug delivery comprises a capsule including a first chamber containing a viscous liquid pharmaceutical composition and a second chamber containing an osmotic agent, the first chamber having an opening through which the pharmaceutical composition can be delivered from the first chamber to a location external of the first chamber; a movable separating member positioned in the capsule between the first chamber and the second chamber; a wall of the second chamber including a fluid permeable portion allowing fluid to pass from a surrounding environment into the second chamber; and an incompressible fluid additive located within the second chamber and substantially surrounding the osmotic agent.

In a detailed embodiment of the dosage form for osmotic drug delivery, the viscous liquid pharmaceutical composition comprises an amphiphilic molecule, a non-aqueous liquid solvent, and a pharmaceutically active agent. In a further detailed embodiment, the amphiphilic molecule is selected from lipids, surfactants, amphiphilic block polymers, or amphiphilic proteins or peptides.

In a detailed embodiment of the dosage form for osmotic drug delivery, the lipid is selected from saturated lipid, unsaturated lipid, neutral lipid, or anionic lipid. In a further detailed embodiment, the lipid is selected from phosphatidylcholine (PC), phosphatidylethanolamine (PE), phosphatidylglycerol (PG), phosphosphatidylinositol (PI), phosphatidylserine (PS), phosphatidic acid (PA), or sphingomyelin (SM). In a further detailed embodiment, the neutral lipid is selected from dioleoyl phosphatidylcholine (DOPC), dimyritoylphosphatidylcholine (DMPC), dipalmitoylphosphatidylcholine (DPPC), distearoylphosphatidylcholine (DSPC), egg phosphatidylcholine (egg PC), soy phosphatidylcholine (soy PC), partially or fully hydrogenated phosphatidylcholins (PHSPC or HSPC), palmitoyl-oleoyl phosphatidylcholine (POPC), or stearyloleoylphosphatidylcholin (SOPC). In a further detailed embodiment, the anionic lipid is selected from dioleoy phosphatidylglycerol (DOPG), dimyritoylphosphatidylglycerol (DMPG), dipalmitoylphosphatidylglycerol (DPPG), or distearoylphosphatidylglycerol (DSPG).

In a detailed embodiment of the dosage form for osmotic drug delivery, the non-aqueous liquid solvent is selected from lauryl lactate (LL), lauryl alcohol (LA), benzyl alcohol (BA), benzyl benzoate (BB), 1:1 benzyl benzoate:benzyl alcohol, benzyl alcohol, ethyl hexyl lactate, glycerol formal, tetraglycol (glycofurol; GF), N-1-methyl-2-pyrrolidone (NMP), dimethyl sulfoxide, (DMSO), polyethyleneglycol (e.g., PEG 400), triglycerides (triolein, trilaurin, tricarprin, tricaprylin), ethanol, isopropanol, t-butyl alcohol, cyclohexanol, glycerin, glycerol, α-tocopherol (vitamin E) vegetable oil, sesame oil, soybean oil, cottonseed oil or peanut oil.

The pharmaceutically active agent is selected from a protein, peptide, small molecule drug, lipid drug or prodrug conjugated to lipid, in a further embodiment.

An amphiphilic molecule weight percent can be from about 1 to about 100 weight percent, in a detailed embodiment of the dosage form for osmotic drug delivery. In a further detailed embodiment, a non-aqueous liquid solvent weight percent can be from about 0 to about 99 weight percent. In further detailed embodiments, viscosity of the composition can be from about 1 to about 100,000 poise. A ratio by weight of amphiphilic molecule to non-aqueous liquid solvent can be between about 1 and about 4.

The osmotic agent is in a tabular form and the fluid additive surrounds the tabular osmotic agent, in a detailed embodiment of the dosage form for osmotic drug delivery. The separating member can be a slidable piston. The fluid permeable portion can be a membrane. In a further detailed embodiment, the osmotic agent is a tablet. The fluid additive can be a lubricating liquid for preventing freeze-up of the osmotic agent. The fluid additive can be a gel. In a further detailed embodiment, the fluid additive includes PEG. The osmotic agent includes NaCl.

In a detailed embodiment, the dosage form for the osmotic drug delivery system includes at least one gap between an inner surface of the capsule and the osmotic agent, the fluid additive filling the at least one gap to improve start-up time.

In a further aspect, the present invention provides suspending vehicles that comprise a amphiphilic molecule, a non-aqueous solvent, and a performance modifier. Preferably the suspending vehicles are substantially non-aqueous. Amphiphilic molecules can replace polymers in suspending vehicles in order to build viscosity. Performance modifiers in accordance with the present invention can be used, for example, to improve the stability and/or the flowability of lipid-based suspending vehicles. For example, the use of performance modifiers aids in softening formations, for example, stiff gels, made at exit ports upon contact by the suspending vehicle with aqueous media, for example, bodily fluids. As such, suspending vehicles are preferably flowable upon contact with an aqueous medium. Suspending vehicles are also substantially free of stiff gels upon contact with an aqueous medium.

Another benefit to using performance modifiers, such as co-solvents, is to speed-up preparation of suspending vehicles and suspensions due to increased solubility of the amphiphilic molecule, for example, the lipid, in co-solvents relative to another solvent.

Suspending vehicles comprising performance modifiers can exhibit improved rheological properties as compared to suspending vehicles which do not contain the performance modifier. For example, performance modifiers can be useful for reducing viscosity variations over small composition variations. In a preferred embodiment, the suspending vehicle has a change in viscosity of less than or equal to a factor of 10 in combination with a 10% by weight change in amount of the amphiphilic molecule in the suspending vehicle.

In some embodiments, the amphiphilic molecule in the suspending vehicle preferably comprises a phospholipid. Lipids include, but are not limited to, dioleoyl phosphatidylcholine (DOPC), dimyritoylphosphatidylcholine (DMPC), dipalmitoylphosphatidylcholine (DPPC), distearoylphosphatidylcholine (DSPC), egg phosphatidylcholine (egg PC), soy phosphatidylcholine (soy PC), partially hydrogenated phosphatidylcholins (PHSPC), fully hydrogenated phosphatidylcholins (HSPC), palmitoyl-oleoyl phosphatidylcholine (POPC), or stearyloleoylphosphatidylcholine (SOPC).

Suspending vehicles have a weight ratio of the non-aqueous solvent to the performance modifier that is, for example, preferably from about 1:3 to about 1:0.001, more preferably from about 1:1 to about 1:0.001, and even more preferably from about 1:0.33 to about 1:0.001. A weight ratio of the amphiphilic molecule to the performance modifier is preferably from about 0.18:1 to about 5.7:1, more preferably from about 0.43:1 to about 2.33:1, and even more preferably from about 0.67:1 to about 1.5:1. A weight ratio of the amphiphilic molecule to a combination of the performance modifier and the non-aqueous solvent is preferably from about 0.05:1 to about 19:1, more preferably from about 0.5:1 to about 1.5:1, even more preferably from about 0.75:1 to about 1.22:1.

In a preferred embodiment of a suspending vehicle, the lipid comprises dioleoyl phosphatidylcholine (DOPC), the non-aqueous solvent comprises α-tocopherol, and the performance modifier comprises ethanol, sesame oil, ethyl acetate, or combinations thereof.

Kits in accordance with the present invention comprise a suspending vehicle and instructions for suspending or dispersing a pharmaceutically active agent therein to create a pharmaceutical suspension. Other kits further comprise a dosage form and instructions for loading the dosage form with the pharmaceutical suspension.

Pharmaceutical suspensions can be created by adding a pharmaceutically active agent to suspending vehicles of the present invention. Pharmaceutical suspensions can also be added to desirable dosage forms, for example, dosage forms that are driven by pumps, for example, osmotic delivery devices.

Pharmaceutical suspensions in accordance with the present invention comprise a pharmaceutically active agent suspended or dispersed in a suspending vehicle, wherein the suspending vehicle comprises an amphiphilic molecule, a non-aqueous solvent, and a performance modifier. Suspending vehicles have a viscosity of from about 1 to about 1,000,000 poise, preferably the viscosity is from about 5 to about 100,000 poise.

Although any desirable pharmaceutically active agent may be stable in the suspending vehicles of the present invention, in preferred embodiments, the pharmaceutically active agent comprises ω-interferon.

Preferably, the dosage forms used in conjunction with the present invention have an osmotic pump. In other embodiments, the dosage forms comprise a wall that maintains its physical and chemical integrity during the life of the dosage form and is substantially impermeable to a pharmaceutical suspension; another wall that is partially permeable to an exterior fluid; a compartment defined by the wall; and an exit port in the wall in communication with the compartment; and wherein the pharmaceutical suspension is positioned within the compartment.

In some examples, the pharmaceutical suspension is flowable through the exit port upon contact with an aqueous medium, preferably under normal operating conditions of the osmotic pump. The pharmaceutical suspensions can also be substantially free of stiff gels upon contact with an aqueous medium. In other embodiments, the pharmaceutical suspensions are substantially homogeneous for at least 3 months.

Kits in accordance with the present invention comprise a dosage form containing a pharmaceutical suspension and instructions for administering the dosage form.

Methods in accordance with the present invention comprise identifying an amphiphilic molecule; identifying a non-aqueous solvent; identifying a performance modifier; mixing the amphiphilic molecule, the non-aqueous solvent, and the performance modifier to create a suspending vehicle. In some embodiments, the performance modifier improves rheological properties of the suspending vehicle as compared to a suspending vehicle which does not contain the performance modifier. Other methods include substantially dissolving or dispersing the amphiphilic molecule in the performance modifier to create a mixture; and combining the non-aqueous solvent with the mixture to create a suspending vehicle. Additionally, in other methods, the amphiphilic molecule dissolves more quickly in a combination of the non-aqueous solvent and the performance modifier as compared to dissolution in only the non-aqueous solvent.

In some methods, the mixture is vortexed. In other embodiments, it is preferable to heat the suspending vehicle to a temperature of from about 100° C. to about 120° C.

Methods in accordance with the present invention also include administering the dosage form containing pharmaceutical suspensions in accordance with the present invention to a mammal.

BRIEF DESCRIPTION OF THE DRAWINGS

FIG. 12 shows a measure of the average protein released from a delivery device based on piston movement within the device.

DETAILED DESCRIPTION

Figure 1:
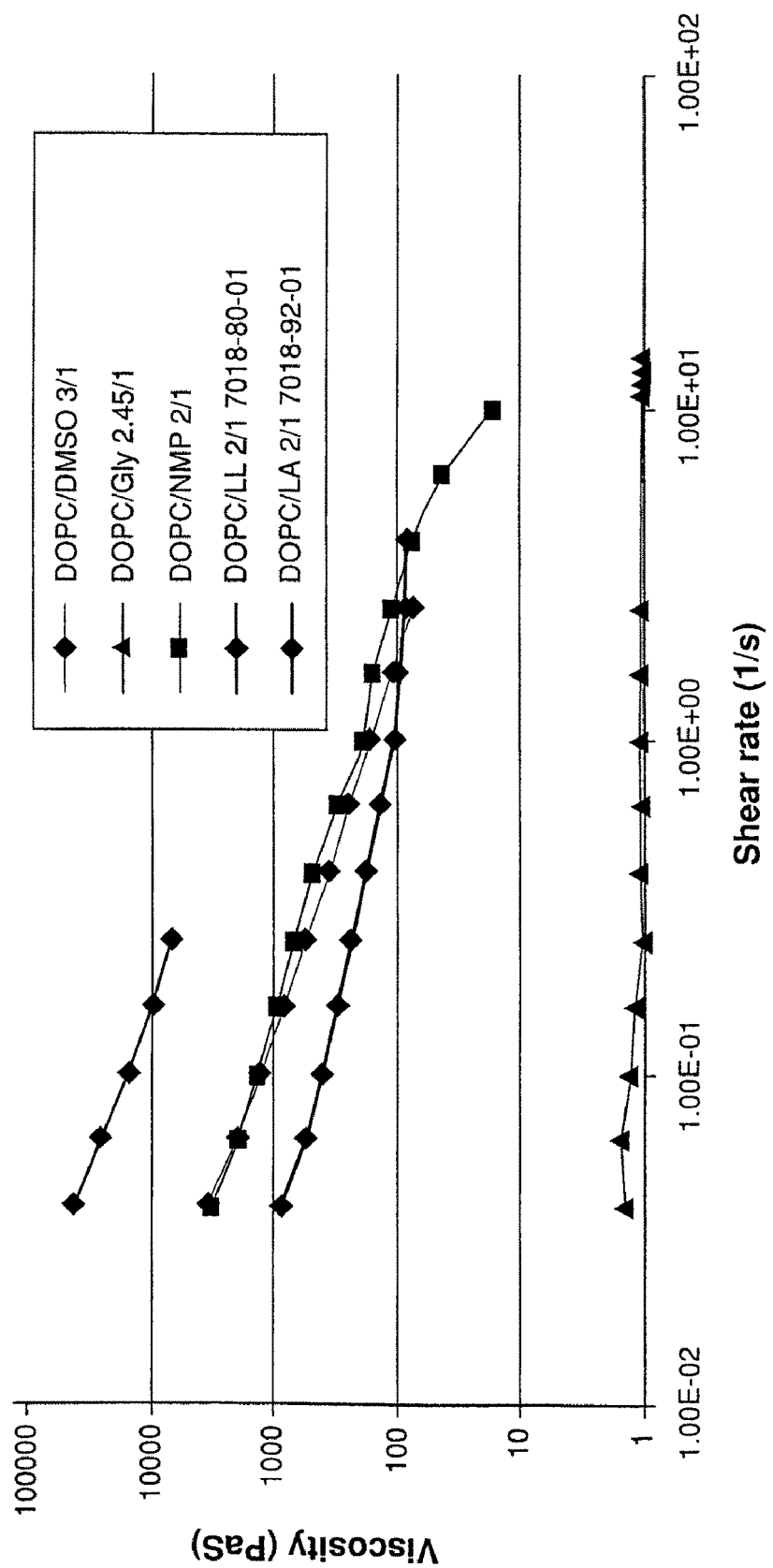
FIG. 1 shows that DOPC formulations can be shear thinning, a phenomena that can ease the manufacturing process of the vehicles.
Figure 2:
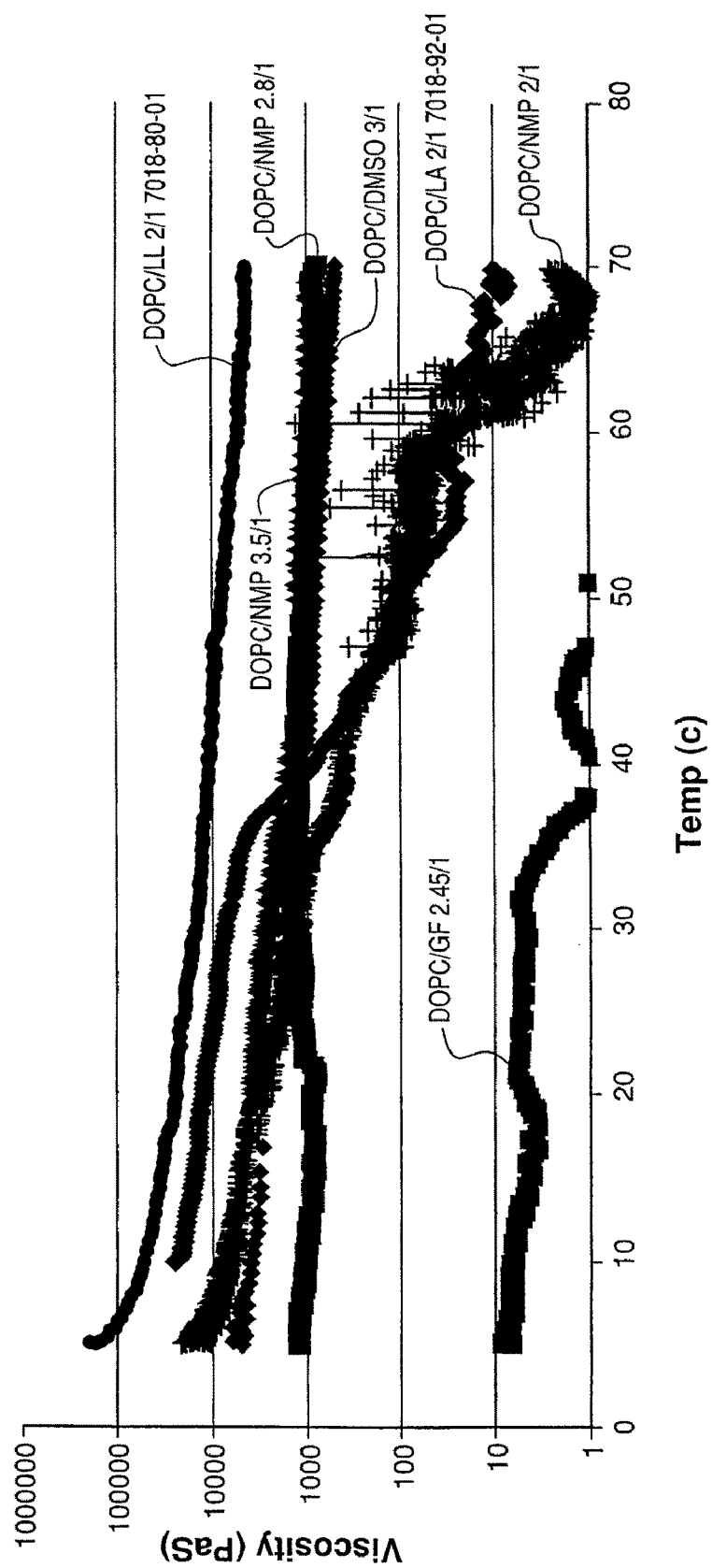
FIG. 2 shows that the viscosity of DOPC formulations is temperature controlled.
Figure 3:
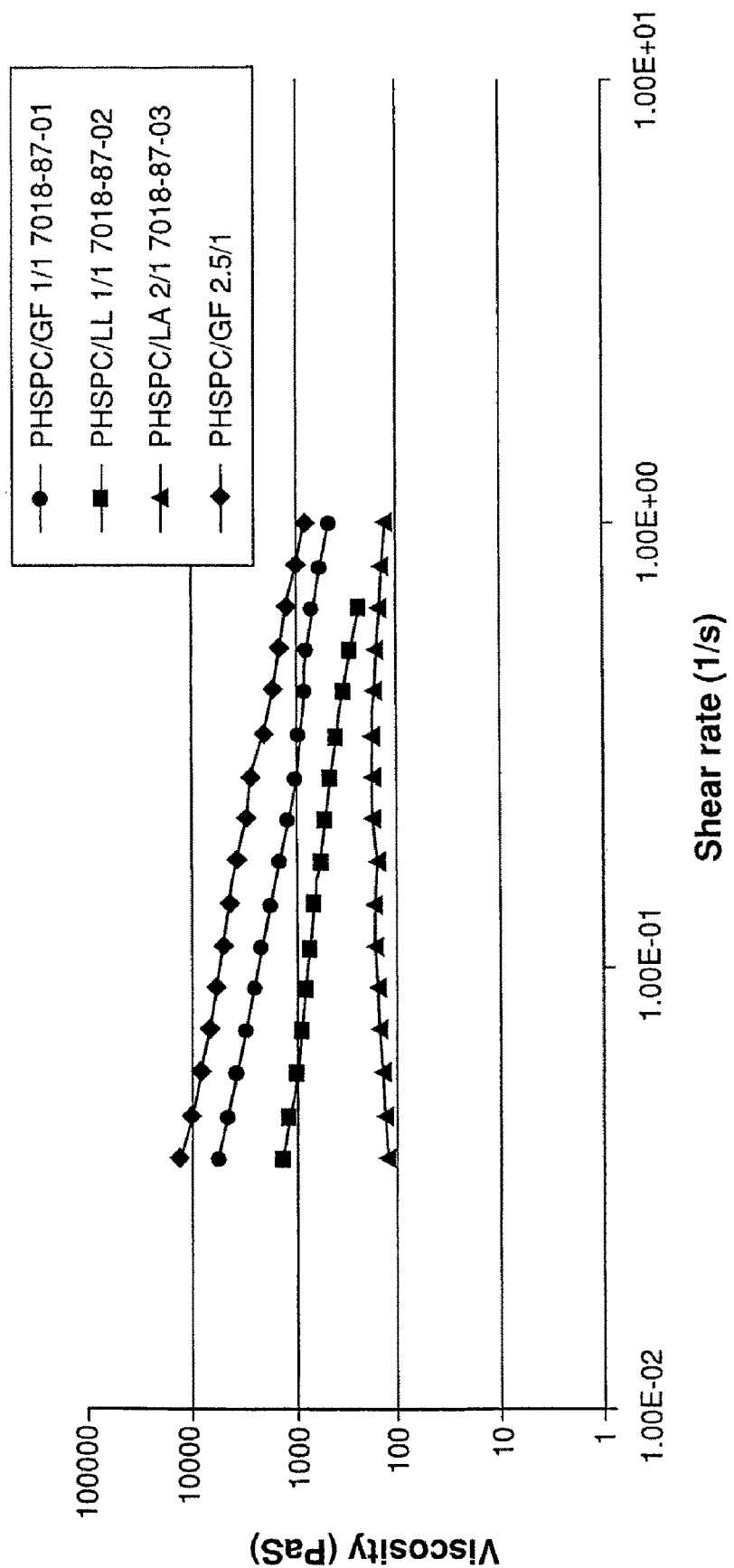
FIG. 3 shows that PHSPC formulations can be shear thinning, a phenomena that can ease the manufacturing process of the vehicles.
Figure 4:
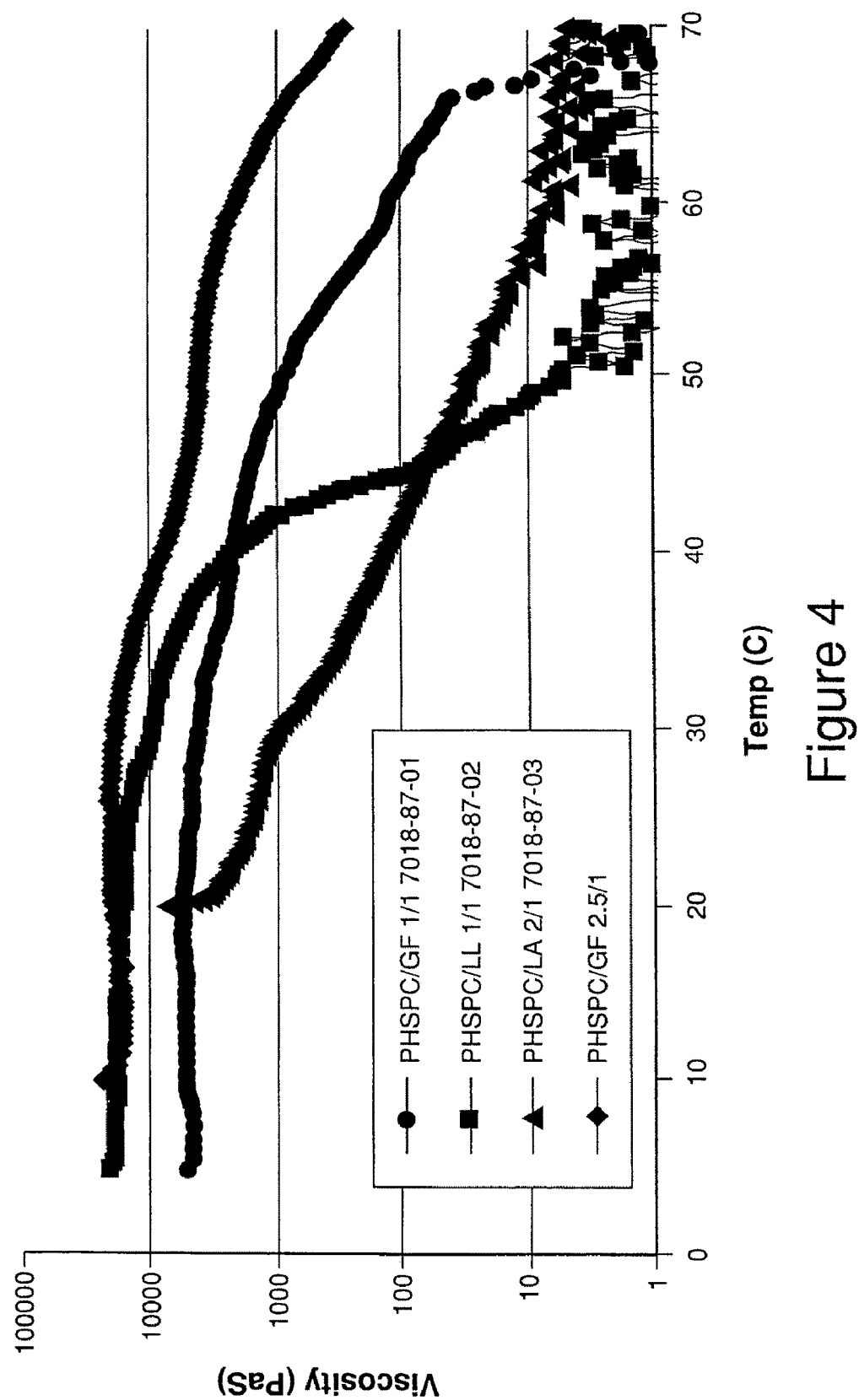
FIG. 4 shows that the viscosity of PHSPC formulations is temperature controlled.
Figure 5:
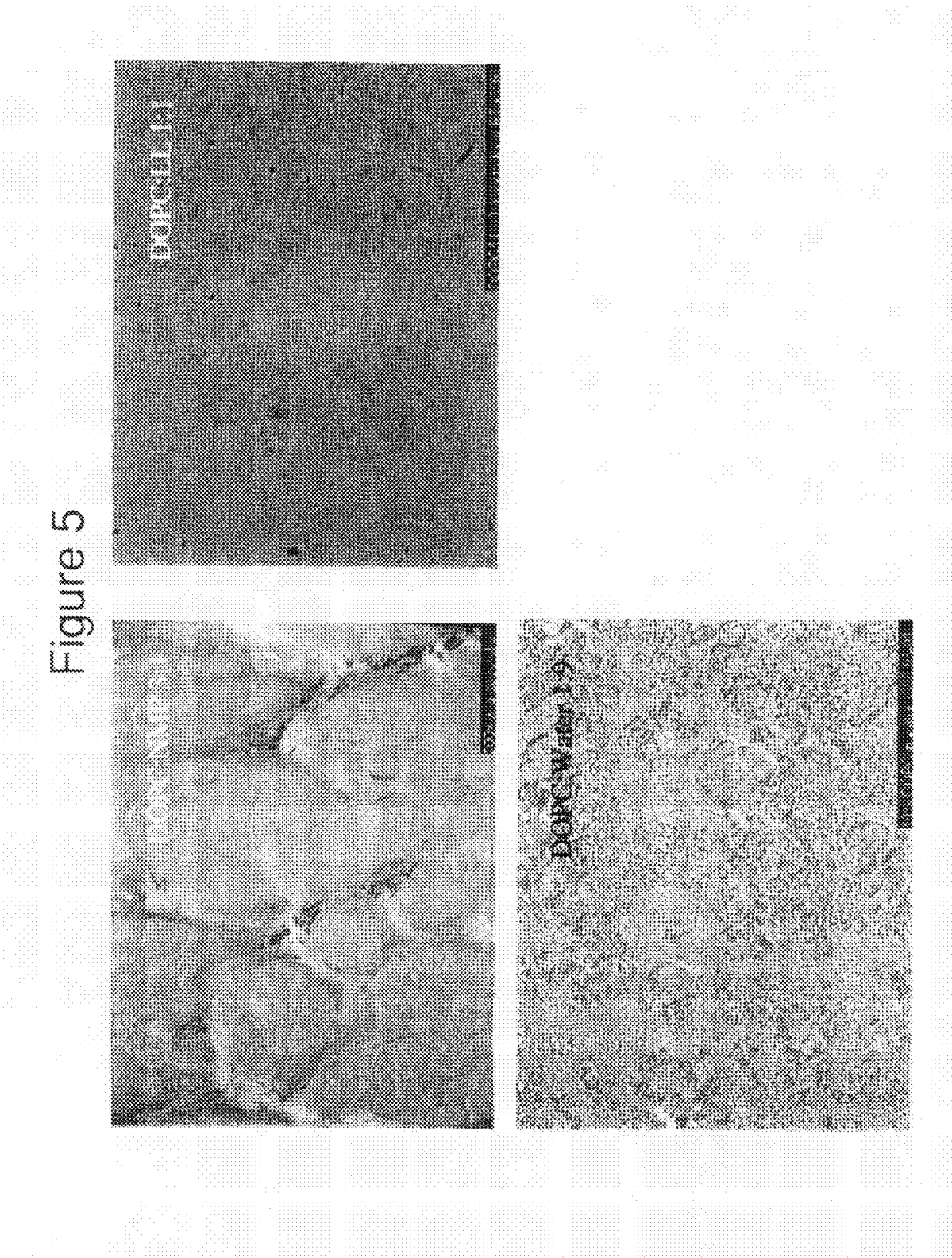
FIG. 5 shows images of DOPC formulations under polarized microscopy.
Figure 6:
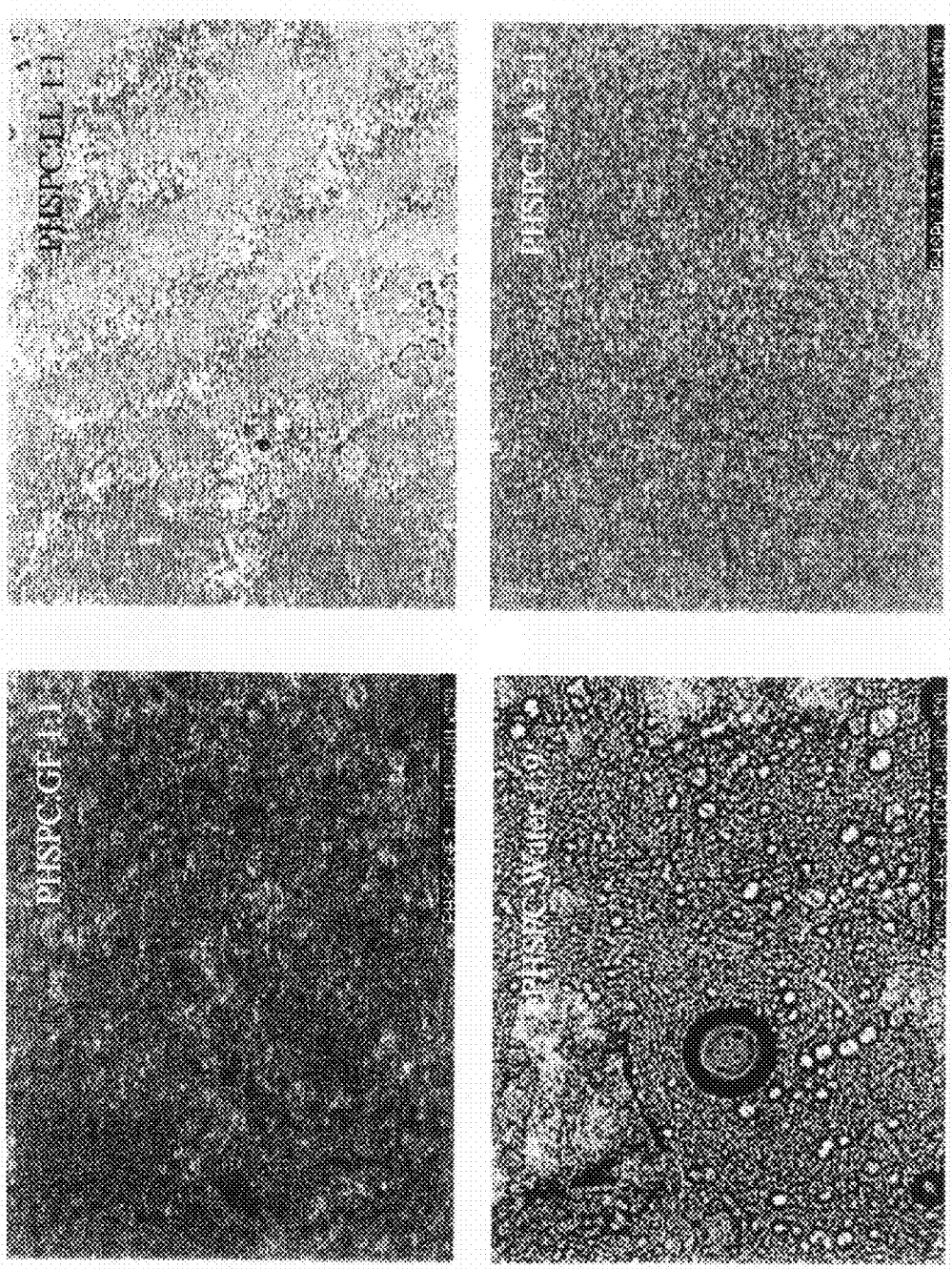
FIG. 6 shows images of PHSPC formulations under polarized microscopy.

A liquid composition in an osmotic drug delivery system of the present invention comprises amphiphilic molecules in combination with a solvent to form liquid compositions with desired properties that exhibit a desired viscosity and that exhibit a desired solvency in water. The viscous liquid compositions are useful for therapeutic drug delivery applications in which the formulation is slowly introduced into an aqueous environment. Amphiphilic molecules include, but are not limited to, lipids, surfactants, amphiphilic block polymers, or amphiphilic proteins or peptides.

Dynamic transfer mechanisms occur at the interface between non-aqueous liquid viscous drug suspensions as they pass through a conduit of a drug delivery device into an aqueous environment. Water ingress into the conduit can occur by one or all of several potential mechanisms: back diffusion, partitioning or percolation through the packed particles of the dispersed phase. Lipids exhibit solubility or dispersion in a wide range of non-aqueous liquid solvents. The wide range of solubility or dispersity lends to the use of lipids in formulation of viscous liquid drug compositions. When the viscous liquid composition contacts the aqueous environment, lipids can form small vesicles of one or all several potential forms: bilayers (multilamellar vesicles, unilamellar vesicles/liposomes), micelles or inverted micelles (hexagonal structure) in water. This self-assembly characteristic allows for viscous delivery vehicles to be formed while at the same time limiting precipitation or the formation of highly viscous materials at the formulation/water interface.

Polymers, for example PVP, exhibit solubility in a wide range of non-aqueous liquid solvents as well, but they can also be quite soluble in water. As a result, highly viscous PVP/water gels can be produced in the non-aqueous liquid solvent/water interface. These viscous gels can occlude the delivery conduit, interfering with performance of the delivery device. In addition, while polymer gels form in the diffusion moderator of DUROS osmotic drug delivery system, they can precipitate and plug a conduit of the system, thus interfering with the release of the drug or therapeutic protein.

Amphiphilic molecules, e.g., lipids, in non-aqueous liquid solvents can provide liquid viscous drug and protein delivery systems in an osmotic delivery device. The composition can limit precipitation, aggregation or the formation of highly viscous gels in the solvent/lipid/water interface. Amphiphilic molecules, e.g., lipids, can also provide a less detrimental environment to incorporated therapeutic proteins due to the slower uptake of water after administration. Lipids can also be used as stabilizers for proteins to extend the therapeutic efficacy of the protein drug.

"Non-aqueous liquid solvent" refers to an organic molecule that will form a liquid viscous solution in combination with an amphiphilic molecule in the absence of water. The solvent can be; for example, a non-polar solvent, a protic solvent, such as an alcohol or acid, or an aprotic solvent, a polar solvent of moderately high dielectric constant, which does not contain an acidic hydrogen.

Lipids can be dissolved in various non-aqueous liquid solvents in different ratios to adjust the viscosity of the vehicle from 1-1,000,000 poise. These formulations can be shear thinning, a phenomena that can ease the manufacturing process of the vehicles. In addition, the solvent to be used can be optimized for maximal stability of the protein. In some cases, both lipids and the solvents to be used in the viscous liquid composition are approved for parenteral use by the Food and Drug Administration (FDA). Amphiphilic molecule weight percent in the formulation can range from about 1 to about 100 weight %. Solvent weight percent into the formulation can range from about 0 to about 99 weight %.

The viscous liquid compositions, including a pharmaceutically active agent cam be delivered by an osmotic drug delivery device, for example, U.S. Pat. Nos. 6,132,420; 6,174,547; 6,419,952; 6,551,613, each incorporated herein by reference in their entirety.

Viscous liquid compositions can exhibit the desired solvency in water and can have potential delivery applications in which the formulation is slowly introduced into an aqueous environment. Viscous liquid compositions comprising lipids in non-aqueous liquid solvents can replace the use of polymers such as polyvinyl pyrrolidone (PVP) to build viscosity in suspension vehicles. In an exemplary embodiment of viscous liquid compositions, solvents in which ω-interferon was shown to have a solubility of less than 0.1 mg/mL were combined with the lipid 1,2-Dioleoyl-sn-glycero-3-phosphatidylcholine (DOPC) to form a suspension of ω-interferon in solid particles in a pharmaceutical formulation. The exemplary non-aqueous liquid solvents included, but are not limited to, lauryl lactate (LL), lauryl alcohol (LA), benzyl alcohol (BA), benzyl benzoate (BB), 1:1 benzyl benzoate:benzyl alcohol, benzyl alcohol, ethyl hexyl lactate, glycerol formal, tetraglycol (glycofurol; GF), N-1-methyl-2-pyrrolidone (NMP), dimethyl sulfoxide, (DMSO), polyethyleneglycol (e.g., PEG 400), triglycerides (triolein, trilaurin, tricarprin, tricaprylin), ethanol, isopropanol, t-butyl alcohol, cyclohexanol, glycerin, glycerol, α-tocopherol (vitamin E) vegetable oil, sesame oil, soybean oil, cottonseed oil or peanut oil. The lipid, e.g., DOPC, was soluble over a wide range of solvent-to-lipid ratios. Lauryl lactate (LL) and N-methylpyrrolidone (NMP) as solvents in combination with lipid were chosen for further study.

Lipids can be dissolved in various non-aqueous liquid solvents in different ratios to adjust the viscosity of the vehicle from zero poise to 1,000,000 poise. The formulations can thin with increasing shear, a phenomena that can increase the ease with which the vehicles can be processed. Studies have shown that DOPC in lauryl lactate (LL) and N-methylpyrrolidone (NMP) at weight ratios of 1.5:1 and 3:1 lipid-to-solvent, respectively, have a viscosity of approximately 42,000 and 15,000 poise, respectively, at 37° C. and shear rates of ranging from 0.04-10 sec$^{-1}$. These compositions have been shown to be shear thinning.

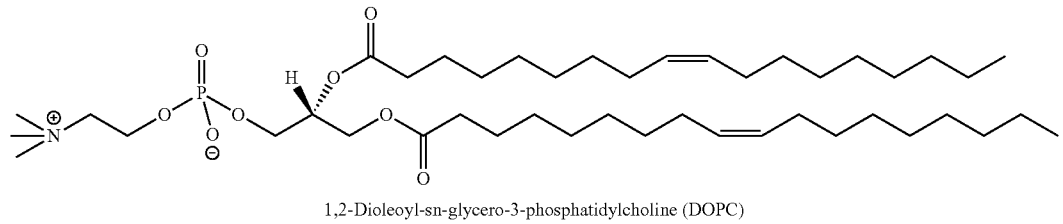

1,2-Dioleoyl-sn-glycero-3-phosphatidylcholine (DOPC)

1,2-Dioleoyl-sn-glycero-3-phosphatidylcholine (DOPC) has a molecular weight of 786.13 kdalton, and a phase transition temperature of −18° C.

The high viscosity and shear thinning properties of lipid/solvent solutions suggest that they can be suitable vehicles for DUROS® implants or OROS® osmotic delivery systems. See, for example, U.S. Pat. Nos. 6,132,420; 6,174,547; 6,419,952; 6,551,613, each incorporated herein by reference in their entirety. The study has determined that ω-interferon in DOPC/solvent compositions, e.g., DOPC/lauryl lactate or DOPC/α-tocopherol, at 40° C. is stable for at least four weeks. The DOPC/solvent compositions can be stable up to 3 months. A dissolution and release rate study has determined that the lipid gels allow the delivery of soluble ω-interferon into an aqueous environment.

"Amphiphilic molecule" refers to a molecule with distinct polar (hydrophilic) and non polar (hydrophobic) regions in the molecule. A "lipid" refers to a heterogeneous group of biological compounds that can contain a large organic cation or anion which possesses a long unbranched hydrocarbon chain, e.g., $H_3C(CH_2)_nCO_2^-M^+$, $H_3C(CH_2)_nSO_3^-M^+$, $H_3C(CH_2)_nN(CH_3)_3^+X^-$ (n>7). The existence of distinct polar (hydrophilic) and non polar (hydrophobic) regions in the molecule can promote the formation of micelles in dilute aqueous solution. "Cationic lipids" have a net positive charge. "Anionic lipids" have a net negative charge. "Neutral lipids" have a net neutral charge.

"Lipid" refers to a heterogeneous group of biological compounds which are sparingly soluble in water, but very soluble in nonpolar solvents. As a class, lipids can be defined by their solubility. They include chemically diverse compounds. "Natural lipids" include, but are not limited to, triacylglycerols, waxes, and terpenes (e.g., monoterpenes, diterpenes, carotenoids or steroids). The more complex lipids include glycolipids and phospholids. Triacylglycerols and waxes are known as saponifiable lipid, whereas terpenes are called non-saponifiable lipid. "Saturated lipids" have all single bonded C—C hydrocarbon chains. "Unsaturated lipids" have one or more doubled bonded (C=C) or triple bonded (C≡C) hydrocarbon chains.

"Amphiphilic block polymer" refers to block copolymers such as Pluronic® block copolymer surfactants, (BASF Corporation, Mount Olive, N.J.; e.g., Pluronic® surfactants or Pluronic® surfactant F-127), or sorbitan esters structurants (e.g., Span® 80, Sigma Aldrich Chemical Co.) can be used, which can function as antifoaming agents, wetting agents, dispersants, thickeners, and emulsifiers. Pluronic® block copolymer surfactants can be based on ethylene oxide and propylene oxide.

"Amphiphilic protein or peptide" refers to a polypeptide chain with distinct polar (hydrophilic) and non polar (hydrophobic) regions in the protein. The tertiary structure of protein is hydrophilic or highly charged (positively or negatively charged) at one region of the protein, and is hydrophobic (non-polar) at another region of the protein.

Amphiphilic molecules useful in the present invention include, but are not limited to, lipid, surfactant, amphiphilic block polymer, or amphiphilic proteins or peptides. Examples of amphiphilic molecules that can be suitable substances for forming a viscous liquid composition are fatty acid esters, e.g., glyceryl monoesters of fatty acids. Other substances which have ability of forming a viscous liquid composition can be found among amphiphilic substances such as polar lipids, surfactants and emulsifiers. Examples of glyceryl monoesters of fatty acids include glycerylmonooleate (monoolein) and glycerylmonolinoleate.

The "viscosity" of a fluid refers to resistance of the fluid to shear or flow, and is a measure of the fluid's adhesive/cohesive or frictional properties. This arises because of the internal molecular friction within the fluid producing the frictional drag effect. Viscosity is useful in the study of biopolymers because the addition of large molecules to a solvent increases its viscosity; the increase depends on the concentration, size, and structure of the polymer. Motion in one layer of a fluid causes motion in adjoining layers. To move layers with different relative velocities requires a force: the more viscous, the more force. Dynamic viscosity is also termed "absolute viscosity" and is the tangential force per unit area required to move one horizontal plane with respect to the other at unit velocity when maintained a unit distance apart by the fluid. The theoretical unit of viscosity is the Poise.

Fatty acid esters capable of forming a viscous liquid composition comprise a fatty acid component and a hydroxy-containing component wherein the fatty acid component of the fatty acid ester is a saturated or unsaturated fatty acid having a total number of carbon atoms of from $C_6$ to $C_{26}$. Specific examples of saturated fatty acid moieties in the fatty acid esters according to the invention include, but are not limited to, moieties of caproic acid, caprylic acid, capric acid, lauric acid, myristic acid, palmitic acid, stearic acid, arachidic acid, and behenic acid. Specific examples of unsaturated fatty acid moieties in the fatty acid esters according to the invention include, but are not limited to, moieties of palmitoleic acid, oleic acid, linoleic acid, linolenic acid, and arachidonic acid. Further embodiments of fatty acid esters for use in compositions according to the invention include, but are not limited to, fatty acid esters of polyhydric alcohols, fatty acid esters of hydroxycarboxylic acids, fatty acid esters of monosaccharides, fatty acid esters of glycerylphosphate derivatives, fatty acid esters of glycerylsulfate derivatives, and mixtures thereof. In those cases where the hydroxy-containing component of the fatty acid ester is polyvalent, the hydroxy-containing component can be partially or totally esterified with a fatty acid component or with mixtures of fatty acid components.

The polyhydric alcohol component of the fatty acid ester for use, in compositions according to the invention is preferably selected from the group consisting of glycerol, 1,2-propanediol, 1,3-propanediol, diacylgalactosylglycerol, diacyldigalactosylglycerol, erythritol, xylitol, adonitol, arabitol, mannitol, and sorbitol. The fatty acid esters formed from such polyhydric alcohols can be mono- or polyvalent such as, e.g., divalent, trivalent, etc. In particular fatty acid monoesters have proved to have bioadhesive properties and can be fatty acid esters for use in compositions according to the invention. The position of the polyvalent alcohol on which the ester bond(s) is (are) established can be any possible position. In those cases where the fatty acid ester is a diester, triester, etc. the fatty acid components of the fatty acid ester can be the same or different. In a detailed aspect of the present invention, the polyhydric alcohol component can be glycerol.

Further examples of fatty acid esters for use in compositions according to the invention and wherein the hydroxy-containing component is a polyhydric alcohol include, but are not limited to, glycerylmonooleate, glycerylmonolinoleate, glycerol monolinoleate, and mixtures thereof. These fatty acid esters have bioadhesive properties useful in the viscous liquid compositions described herein. In those cases where the fatty acid ester for use in compositions according to the present invention is formed between a hydroxycarboxylic acid (or a derivative thereof) and a fatty acid (or a derivative thereof), the hydroxycarboxylic acid component of the fatty acid ester is preferably selected from the group consisting of malic acid, tartaric acid, citric acid, lactic acid, and sorbic acid. An example of a fatty acid ester for use in compositions according to the invention is a fatty acid monoester of citric acid.

The hydroxy-containing component of a fatty acid ester for use in compositions according to the present invention can also be a saccharide, such as a monosaccharide such as, e.g., glucose, mannose, fructose, threose, gulose, arabinose, ribose, erythrose, lyxose, galactose, sorbose, altrose, tallose, idose, rhamnose, or allose. In those cases where the hydroxy-containing component is a monosaccharide, the fatty acid ester is preferably a fatty acid monoester of a monosaccharide selected from the group consisting of sorbose, galactose, ribose, and rhamnose. The hydroxy-containing component of a fatty acid ester for use in the viscous liquid compositions can also be a glycerylphosphate derivative such as, e.g., a phospholipid selected from, phosphatidylcholine (PC), phosphatidylethanolamine (PE), phosphatidylglycerol (PG), phosphatidylinositol (PI), phosphatidylserine (PS), phosphatidic acid (PA), or sphingomyelin (SM) or diphosphatidylglycerol. Phospholipids can further include DEPE (1,2 dielaidoyl-sn-glycerol-3-phosphoethanolamine) and DMPE (PEG 550) (1,2-dimyristoyl-sn-glycero-3-phosphoetiianolainine-N-(polyethylene glycol)550).

Compounds having a phospholipid moiety further include compounds wherein the fatty acid ester is a fatty acid ester of a glycerylphosphate derivative, and the fatty acid component is selected from the group consisting of lauric acid, myristic acid, palmitic acid, stearic acid, oleic acid, linoleic acid, linolenic acid, and behenic acid. Examples of such useful fatty acid esters can be dilauryl phosphatidylcholine, dioleoyl phosphatidylcholine (DOPC), dimyritoylphosphatidylcholine (DMPC), dipalmitoylphosphatidylcholine (DPPC), distearoylphosphatidylcholine (DSPC), egg phosphatidylcholine (egg PC), soy phosphatidylcholine (soy PC), partially or fully hydrogenated phosphatidylcholins (PHSPC or HSPC), palmitoyl-oleoyl phosphatidylcholine (POPC), stearyloleoylphosphatidylcholin (SOPC), dibehenoyl phosphatidylcholine, dimyristyl phosphatidylethanolamine, dipalmitoyl phosphatidylethanolamine, dioleoyl phosphatidylglycerol (DOPG), dimyristoylphosphatidylglycerol (DMPG), dipalmitoylphosphatidylglycerol (DPPG), or distearoylphosphatidylglycerol (DSPG), dilauryl phosphatidylglycerol, dipalmitoyl phosphatic acid and mixtures thereof.

Compounds that can be useful as amphiphilic molecules include, but are not limited polyethyleneglycol (PEG)-lipid compound selected from mPEG-DPPE, mPEG-DMPE, mPEG-DSPE, or mPEG-ceramide-DSPE, and Pluronic® block copolymer surfactants, selected from PLURONIC® 17R2 surfactant, PLURONIC® 17R4 surfactant; PLURONIC® 25R2 surfactant, PLURONIC® 25R4 surfactant, PLURONIC® 31R1 surfactant, PLURONIC® F108 cast solid surfactant, PLURONIC® F108 NF cast solid surfactant, PLURONIC® F108 NF prill surfactant, PLURONIC® F108 pastille surfactant, PLURONIC® F108 surfactant prill, PLURONIC® F127 cast solid surfactant, PLURONIC® F127 NF 500BHT surfactant prill, PLURONIC® F127 NF cast solid surfactant, PLURONIC® F127 NF prill surfactant, PLURONIC® F127 surfactant prill, PLURONIC® F127NF 500BHT cast solid surfactant, PLURONIC® F38 cast solid surfactant, PLURONIC® F38 surfactant pastille, PLURONIC® F68 LF pastille surfactant, PLURONIC® F68 LF cast solid surfactant, PLURONIC® F68 NF cast solid surfactant, PLURONIC® F68 NF prill surfactant, PLURONIC® F68 prill surfactant, PLURONIC® F68 surfactant, PLURONIC® F68 surfactant pastille, PLURONIC® F77 cast solid surfactant, PLURONIC® F77 MICRO-pastille surfactant, PLURONIC® F87 cast solid surfactant, PLURONIC® F87 NF cast solid surfactant, PLURONIC® F87 NF prill surfactant, PLURONIC® F87 prill surfactant, PLURONIC® F88 cast solid surfactant, PLURONIC® F88 prill surfactant, PLURONIC® F88 surfactant pastille, PLURONIC® F98 cast solid surfactant, PLURONIC® F98 prill surfactant, PLURONIC® L10 surfactant, PLURONIC® L101 surfactant, PLURONIC® L121 surfactant, PLURONIC® L31 surfactant, PLURONIC® L35 surfactant, PLURONIC® L43 surfactant, PLURONIC® L44 NF surfactant, PLURONIC® L44 surfactant, PLURONIC® L61 surfactant, PLURONIC® L62 LF surfactant, PLURONIC® L62 surfactant, PLURONIC® L62D surfactant, PLURONIC® L64 surfactant, PLURONIC® L81 surfactant, PLURONIC® L92 surfactant, PLURONIC® N-3 surfactant, PLURONIC® P103 surfactant, PLURONIC® P104 surfactant, PLURONIC® P105 surfactant, PLURONIC® P123 surfactant, PLURONIC® P65 surfactant, PLURONIC® P84 surfactant, PLURONIC® P85 surfactant, PLURONIC® F 127 micro pastille.

Compounds that can be useful as non-aqueous liquid solvent include, but are not limited to, lauryl lactate (LL), lauryl alcohol (LA), benzyl alcohol (BA), benzyl benzoate (BB), 1:1 benzyl benzoate:benzyl alcohol, benzyl alcohol, ethyl hexyl lactate, glycerol formal, tetraglycol (glycofurol; GF), N-1-methyl-2-pyrrolidone (NMP), dimethyl sulfoxide, (DMSO), polyethyleneglycol (e.g., PEG 400), triglycerides (triolein, trilaurin, tricarprin, tricaprylin), ethanol, isopropanol, t-butyl alcohol, cyclohexanol, glycerin, glycerol, α-tocopherol (vitamin E) vegetable oil, sesame oil, soybean oil, cottonseed oil or peanut oil.

Block copolymer surfactants (BASF Corporation, Mount Olive, N.J.; e.g., Pluronic® surfactants or Pluronic® surfactant F-127), or sorbitan esters structurants (e.g., Span® 80, Sigma Aldrich Chemical Co.) can function as antifoaming agents, wetting agents, dispersants, thickeners, and emulsifiers. The Pluronic® type can be block copolymers based on ethylene oxide and propylene oxide.

Most of the fatty acid esters for use in compositions according to the invention can be chemical compounds which are commercially available or can be prepared by means of esterification procedures involving e.g., reaction of a fatty acid derivative such as, e.g., the corresponding acid chloride with a hydroxy-containing compound (if necessary protected with suitable protection groups) and subsequently isolating the fatty acid ester, if necessary after removal of any protecting group. Many of the commercially available fatty acid esters can be employed in the food industry and in general, no steps are taken in order to obtain an approximately 100% pure fatty acid ester. For example, glycerylmonooleate (Danisco Ingredients A/S, Denmark) is a very pure product containing about 98% w/w monoesters of which more than about 80% w/w (such as about 92% w/w) is glycerylmonooleate. The remaining monoesters can be glycerylmonolinoleate, glyceryl monopalmitate and glyceryl monostearate. The fatty acid ester products for use in compositions according to the invention can thus be mixtures of fatty acid esters. Examples of fatty acid esters with bioadhesive properties as well as an excellent ability of forming a viscous liquid composition can be glyceryl monoesters of fatty acids. Specific examples include glycerylmonooleate (monoolein) and glycerylmonolinoleate.

The stability of the viscous liquid composition comprising an amphiphilic molecule and solvent is considerably enhanced, such as resulting in a storage stability of at least 2 years at 25° C., and at least 1 month at 40° C. The fatty acid ester product fulfills certain purity standards. Thus, the fatty acid ester product used for the preparation of the composition should contain at the most 4% of saturated fatty acid ester and should preferably contain at least 88% of fatty acid ester, more preferably at least 89%, such as at least 90% or at least 91%, in particular at least 92%, of fatty acid ester.

The amphiphilic molecule, e.g., lipid, is normally present in an amount of at least about 1% to about 100% by weight, calculated on the total composition, such as at least 25% or at least 50%, or at least 75%, or at least 100% by weight, calculated on the total composition, and a preferred amount is often in the range of 25-90% such as 40-90% by weight, in particular, 40-85%, 45-80% or 50-75% by weight, calculated on the total composition.

Normally, the concentration of the non-aqueous liquid solvent in a composition according to the invention is about 0% to about 99% by weight, at least about 10% by weight such as, e.g., at least 20%, 30%, 40%, 50%, 60%, or 70% by weight, or up to 99% by weight calculated on the composition.

In other terms, the concentration of the non-aqueous liquid solvent in the composition is in a range corresponding to from about 0% to about 99% such as, e.g., about 15%-85%, about 20%-80%, about 25%-75%, about 25%-70%, about 25%-65%, about 25%-60%, about 25%-55%, or about 25%-50% by weight based on the total composition.

Formation of the viscous liquid composition, in addition to comprising an amphiphilic molecule, a non-aqueous solvent, and a pharmaceutically active agent, can further comprise an amphiphilic substance having a molecular weight of, at most, 2000 daltons, or an emulsifier or a surfactant. Tenside surfactants (anionic, cationic, non-ionic like e.g., sorbitan esters, sorbitan macrogol esters (polysorbates)), polar lipids, glycolipids, lecithins, palmitoyl muramic acid (PMA), substances having surface active properties like e.g., certain cellulose derivatives, sorbitan oleate, sorbitan laurate, lanolin and derivatives thereof and ethoxylated derivatives of lanolin (Aqualose W20, Aqualose L30 and Aqualose L75) are also examples of suitable structurants for use in compositions according to the invention. Sorbitan esters can be series of mixtures of partial esters of sorbitol and its mono- and dianhydrides with fatty acids.

Examples of suitable sorbitan esters for use as structurants in a composition according to the invention can be: sorbitan di-isostearate, sorbitan dioleate, sorbitan monoisostearate, sorbitan monolaurate, sorbitan monooleate (e.g., Span® 80, Sigma Aldrich Chemical Co.), sorbitan monopalmitate, sorbitan monostearate, sorbitan sesqui-isostearate, sorbitan sesquioleate (e.g., Span® 83), sorbitan trioleate, sorbitan sesquistearate, sorbitan tri-isostearate, sorbitan tristearate, sorbitan tristearate.

Polyoxyethylene sorbitan fatty acid esters (polysorbates) can be a series of fatty acid esters or sorbitol and its anhydrides copolymerized with approximately 20 moles of ethylene oxide for each mole of sorbitol and its anhydrides. Examples of suitable polysorbates for use in the present context can be: polysorbate 20, polysorbate 21, polysorbate 40, polysorbate 60, polysorbate 61, polysorbate 65, polysorbate 80, polysorbate 81, polysorbate 85, polysorbate 120

In a further embodiment, suitable amphiphilic molecules for use in a viscous liquid composition include tocopherols. "Tocopherols" refers to all vitamin E or vitamin E-like substances, derivatives and analogs thereof. The term includes all tocol and tocotrienol derivatives such as e.g., methyl tocol. More specifically, in the present context, a tocopherol is selected from the group consisting of p-tocopherols, sorbitan esters of tocopherols, d-α-tocopherol, d,l-α-tocopherol, d-α-tocopherol acetate, d,l-α-tocopherol acetate, d-α-tocopherol succinate, d,l-α-tocopherol succinate, d-α-tocopherol nicotinate, d,l-α-tocopherol nicotinate, tocopherylpolyethylene glycol succinate such as d-α-tocopherylpolyethylene glycol succinate or d,l-α-tocopherylpolyethylene glycol succinate, and derivatives such as fatty acid ester derivatives and analogues thereof. Tocopherols for use in a composition according to the present invention can be d-a-30. In a further detailed embodiment, tocopherylpolyethylene glycol 1000 succinate (in the following denoted vitamin E TPGS or simply TPGS) or d,l-α-tocopherylpolyethylene glycol 1000 succinate can be suitable amphiphilic molecules.

Fatty acid esters can be capable of forming various crystalline phases upon contact with a hydrophilic medium such as water or glycerol. The fatty acid esters also show bioadhesive properties. Viscous liquid composition can be a cubic (three cubic liquid crystalline phases are well-characterized: i) the body-centered lattice, ii) the primitive diamond lattice, and iii) the gyroid), reverse cubic, hexagonal, reverse hexagonal, lamellar, micellar or reverse micellar phase. By the term "cubic liquid crystalline phase" herein is meant a thermodynamically stable, viscous and optically isotropic phase made of a suitable substance such as, e.g., a fatty acid ester and a liquid medium such as, e.g., a viscous liquid medium or an aqueous medium. The cubic liquid crystalline phase is contemplated to be build up of closed reversed micelles. The term "viscous liquid medium" includes media comprising an amphiphilic molecule and a non-aqueous liquid solvent. The term "aqueous medium" includes media containing water or another hydrophilic and water-miscible substance such as, e.g., glycerol. The terms "hexagonal phase" and "reverse hexagonal phase", respectively, are used herein to describe thermodynamically stable, viscous and optically anisotropic phases characterized by long-range order in two dimensions and made of a suitable substance such as, e.g., a fatty acid ester and a liquid medium such as, e.g., a viscous liquid medium or an aqueous medium. The term "lamellar phase" is characterised by a long-range order in one dimension. The lamellar structure is the origin of liposomes having spherical shells of lipid bilayers. The various liquid crystalline phases can be detected and identified by use of polarized light or by means of X-ray diffraction pattern analysis. The cubic liquid crystalline phase is normally the preferred phase in the compositions of the invention, but also, e.g., the reverse hexagonal and the reverse cubic liquid crystalline phase can be a liquid crystalline phase in the compositions according to the invention.

Pharmaceutically Active Agents

"Pharmaceutically active agent" refers to any biologically or pharmacologically active substance or antigen-comprising material; the term includes drug substances which have utility in the treatment or prevention of diseases or disorders affecting animals or humans, or in the regulation of any animal or human physiological condition and it also includes any biologically active compound or composition which, when administered in an effective amount, has an effect on living cells or organisms. The pharmaceutically active agent includes, but is not limited to a protein, peptide, small molecule drug, lipid drug or nucleic acid drug (e.g., DNA, RNA, antisense, ribozyme, DNAzyme.

Examples of active substances of particular importance with respect to all aspects of the invention can be the so-called antiherpes virus agents which have been or are developed for the treatment of herpes virus infections [herpes simplex virus types 1 and 2 (HSV-1 and HSV-2), varicella zoster virus (VZV), cytomegalovirus (CMV), Epstein-Barr virus (EBV)]. The antiherpes virus agents include antiviral drugs and prodrugs thereof, such as nucleosides, nucleoside analogues, phosphorylated nucleosides (nucleotides), nucleotide analogues and salts, complexes and prodrugs thereof; e.g., guanosine analogues, deoxyguanosine analogues, guanine, guanine analogues, thymidine analogues, uracil analogues and adenine analogues. Antiherpes virus agent for use either alone or in combination in a composition according to the present invention can be selected from acyclovir, famciclovir, deciclovir, penciclovir, zidovudin, ganciclovir, didanosin, zalcitabin, valaciclovir, sorivudine, lobucavir, brivudine, cidofovir, n-docosanol, ISIS-2922, and prodrugs and analogues thereof. Details concerning active substances suitable for use in connection with the present invention as well as a description of other active substances are given below.

As mentioned above, an important example of an active substance is an antiviral drug, such as a nucleoside or a nucleoside analogue, e.g., selected from acyclovir, famciclovir, deciclovir, penciclovir, zidovudin, ganciclovir, didanosin, zalcitabin, valaciclovir, sorivudine, lobucavir, brivudine, cidofovir, n-docosanol, ISIS-2922 and salts and prodrugs thereof. However, also a large number of other drugs which in themselves have a low solubility as deemed herein or the salts, esters, prodrugs or precursors of which have a low solubility can be important active substances in the compositions of the invention. Furthermore, there is also a large number of drugs which advantageously can be incorporated in a composition according to the invention, either as the sole active substance (provided the solubility criteria can be fulfilled) or in combination with another active substances. In the following is listed a number of active substances which either alone or in combination can be incorporated in a composition according to the present invention. In particular a combination of an anti-herpes virus agent and a glucocorticosteroid is of importance.

Examples of drugs which can be of particular importance in connection with application to skin or mucosal surfaces are: Acyclovir, famciclovir, ribavirin, zidovudin, ganciclovir, didanosin, zalcitabin, valaciclovir amantadin, rimantadin foskarnet idoxuridin fluoruracil interferons and variants thereof, including α-interferon, β-interferon, γ-interferon, interferon, tromantadin, lentinan, levofloxacin, stavudine, tacrine, vesnarinone, ampligen, atevirdine, delavirdine, hydroxyurea, indinavir sulfate, interleukin-2 fusion toxin, seragen, lamivudine, lidakol, nevirapine, onconase, saquinavir, topotecan, verteporfin, viraplex, CMV immunoglobulin, Efalith, epervudine, podophyllotoxin, proxigermanium, rifabutin, bromovinyldeoxyuridine, ukrain, cidofovir, imiquimod, lamivudine, sorivudine, viraplex afovirsen amonafide hypericin, provir, temoporfin, apbidicolin glycinate, ibobucavir, virend, AL-721, ampligen, arildone, brivudine, CD4,2-deoxy-D-glucose, desciclovir, dichloroflavan, didanosine, ditiocarb Sodium edoxudine, enviroxime, fiacitabine, inosine Pranobex, peptide T stavudine tribavirin trifluridine vidarabine zalcitabine, miconazol fucidin, erythromycin macrolides, NSAlD's, peptides insulin, polymycin, myperizin, antibiotics, nicotine sucralfate, sucrose octasulfate, salicylic acid, urea, benzoylperoxide minoxidil, heparinoid, methotrexate, ciclosporin.

A listing of substances of potential interest comprises substances of the following groups: sodium fluoride, anti-inflammatory drugs such as, e.g., ibuprofen, indomethacin, naproxen, diclofenac, tolfenamic acid, piroxicam, and the like; narcotic antagonists such as, e.g., naloxone, nalorphine, and the like; antiparkinsonism agents such as, e.g., bromocriptine, piperidin, benzhexyl, benztropine, and the like; antidepressants such as, e.g., imipramine, nortriptyline, pritiptylene, and the like; antibiotic agents such as, e.g., clindamycin, erythromycin, fusidic acid, gentamicin, mupirocien, amfomycin, neomycin, metronidazole, silver sulphadiazine, sulphamethizole, bacitracin, framycetin, polymycin B, acitromycin, and the like; antifungal agents such as, e.g., miconazol, ketoconazole, clotrimazole, amphotericin B, nystatin, mepyramin, econazol, fluconazol, flucytocine, griseoftdvin, bifonazole, amorolfine, mycostatin, itraconazole, terbenafine, terconazole, tolnaftate, and the like; antimicrobial agents such as, e.g., metronidazole, tetracyclines, oxytetracycline, and the like; antiemetics such as, e.g., metoclopramide, droperidol, haloperidol, promethazine, and the like; antihistamines such as, e.g., chlorpheniramine, terfenadine, triprolidine, and the like; antimigraine agents such as, e.g., dihydroergotamine, ergotamine, pizotyhne, and the like; coronary, cerebral or peripheral vasodilators such as, e.g., nifedipine, diltiazem, and the like; antianginals such as, e.g., glyceryl nitrate, isosorbide denitrate, molsidomine, verapamil, and the like; calcium channel blockers such as, e.g., verapamil, nifedipine, diltiazem, nicardipine, and the like; hormonal agents such as, e.g., estradiol, estron, estriol, polyestradiol, polyestriol, dienestrol, diethylstilbestrol, progesterone, dihydroergosterone, cyproterone, danazol, testosterone, and the like; contraceptive agents such as, e.g., ethynyl estradiol, lynestrenol, etynodiol, norethisterone, mestranol, norgestrel, levonorgestrel, desogestrel, medroxyprogesterone, and the like; antithrombotic agents such as, e.g., heparin, warfarin, and the like; diuretics such as, e.g., hydrochlorothiazide, flunarizine, minoxidil, and the like; antihypertensive agents such as, e.g., propanolol, metoprolol, clonidine, pindolol, and the like; corticosteroids such as, e.g., beclomethasone, betamethasone, betamethasone-17-valerate, betamethasone-dipropionate, clobetasol, clobetasol-17-butyrate, clobetasol-propionate, desonide, desoxymethasone, dexamethasone, diflucortolone, flumethasone, flumethasone-pivalate, fluocinolone acetonide, fluocinonide, hydrocortisone, hydrocortisone-17-butyrate, hydrocortisonebuteprate, methylprednisolone, triamcinolone acetonide, budesonide, halcinonide, fluprednide acetate, alklometasonedipropionate, fluocortolone, fluticason-propionate, mometasone-furate, desoxymethasone, diflurason-diacetate; halquinol, cliochinol, chlorchinaldol, fluocinolone-acetonid, and the like; dermatological agents such as, e.g., nitrofurantoin, dithranol, clioquinol, hydroxyquinoline, isotretionin, methoxsalen, methotrexate, tretionin, trioxsalen, salicylic acid, penicillamine, and the like; steroids such as, e.g., estradiol, progesterone, norethindrone, levonorgestrol, ethynodiol, levenorgestrel, norgestimate, gestanin, desogestrel, 3-keton-desogestrel, demegestone, promethoestrol, testosterone, spironolactone, and esters thereof, nitro compounds such as, e.g., amyl nitrates, nitroglycerine and isosorbide nitrates, opioid compounds such as, e.g., morphine and morphine-like drugs such as buprenorphine, oxymorphone, hydromorphone, levorphanol, fentanyl and fentanyl derivatives and analogues, prostaglandins such as, e.g., a member of the PGA, PGB, PGE, or PGF series such as, e.g., misoprostol, dinoproston, carboprost or enaprostil, a benzamide such as, e.g., metoclopramide, scopolamine, a peptide such as, e.g., growth hormone releasing factors, growth factors (epidermal growth factor (EGF), nerve growth factor (NGF), TGF, PDGF, insulin growth factor (IGF), fibroblast growth factor (FGF$\alpha$, FGF$\beta$, etc.), and the like), somatostatin, calcitonin, insulin, vasopressin, interferons, interleukins, e.g., IL-2, IL-12, IL-21, urokinase, serratiopeptidase, superoxide dismutase (SOD), thyrotropin releasing hormone (TRH), luteinizing hormone releasing hormone (LH-RH), corticotrophin releasing hormone (CRF), growth hormone releasing hormone (GHRH), oxytocin, erythropoietin (EPO), colony stimulating factor (CSF), and the like, a xanthine such as, e.g., caffeine, theophylline, a catecholamine such as, e.g., ephedrine, salbutamol, terbutaline, a dihydropyridine such as, e.g., nifedipine, a thiazide such as, e.g., hydrochlorothiazide, flunarizine, others such as, e.g., propanthelin, silver nitrate, enzymes like Streptokinases, Streptodases, vitamins like vitamin A, tretionin, isotretionin, acitretin, vitamin D, calcipotriol, interferon-$\alpha$-2b, selen disulfide, pyrethione. It will be understood that the compositions of the invention can also comprise combinations of active substances, e.g., an active substance together with a potentiator therefor. It will of course also be understood that in the aspects of the invention wherein there is no specific requirement to the active substance, e.g., with respect to solubility, any substance which has a therapeutic or prophylactic activity can be incorporated in the composition.

Pharmaceutically Acceptable Excipients for Use in a Viscous Liquid Composition

An aspect of the invention relates to compositions wherein at least a part of the viscous liquid composition at room temperature can be substituted by certain pharmaceutically acceptable excipients. Addition of a pharmaceutically acceptable excipient to a viscous liquid composition or a precursor composition will normally lead to a disruption in the viscous liquid composition. Therefore, such substance is generally only added in very small concentrations such as, e.g., about 1-5% by weight based on the total composition. Certain pharmaceutically acceptable excipients can be added in much larger concentrations without having any substantially negative influence on the biopharmaceutical properties of the composition. Thus, the concentration of such excipients can be at least about 5% by weight such as, e.g., at least about 8%, 9%, 10%, 15% or 20% by weight.

Examples of suitable pharmaceutically acceptable excipients can be found e.g., among inert diluents or fillers selected from the group consisting of sucrose, sorbitol, sugar, mannitol, microcrystalline cellulose, carboxymethylcellulose sodium, methylcellulose, hydroxypropyl methylcellulose, ethylcellulose, starches including potato starch, calcium carbonate, sodium chloride, lactose, calcium phosphate, calcium sulfate, sodium phosphate, and a polysaccharide such as, e.g., carmellose, a chitosan, a pectin, xanthan gum, a carrageenan, locust bean gum, acacia gum, a gelatin, an alginate, and dextrans and salts thereof.

Examples of suitable pharmaceutically excipients which can be soluble in the second substance or in the liquid crystalline phase are e.g., sorbitan esters such as, e.g., polysorbates; and macrogols. In the present context, solvents like e.g., water, glycerol, alcohols like e.g., ethanol and isopropylalcohol are examples of a liquid medium and are not intended to be examples of soluble pharmaceutically acceptable excipients.

Pharmaceutical Compositions and Routes of Administration

The viscous liquid composition in an osmotic delivery system is intended for parenteral administration and for topical administration to skin or mucosa. Other applications can of course also be relevant such as, e.g., application on dentures, prostheses and application to body cavities such as the oral cavity. The mucosa is preferably selected from oral, nasal, aural, lung, rectal, vaginal, and gastrointestinal mucosa.

A bioadhesive composition for administration according to the invention can also be in the form of a multiple unit composition, in the form of, e.g., a powder. A multiple unit composition can be administered to skin or mucosa, preferably the mucosa is selected from oral, nasal, rectal, aural, vaginal, lung, and gastrointestinal mucosa. Most preferred is a bioadhesive composition intended for administration to the gastrointestinal tract.

Bioadhesive compositions according to the invention for application on skin can comprise a polysaccharide in a concentration of at least 15% w/w, calculated on the total weight of the composition. The polysaccharide is preferably selected from the group consisting of carmelose, chitosan, pectins, xanthan gums, carrageenans, locust bean gum, acacia gum, gelatins, alginates, and dextrans, and salts thereof. The compositions can be easy to apply on the wound and are believed to be able to extract water from the wound and thereby drying the wound. Apart from the active or protective substance and the bioadhesive fatty acid ester substance, the bioadhesive compositions for use according to the invention can comprise pharmaceutically or cosmetically acceptable excipients or additives normally used in pharmaceutical compositions.

The bioadhesive compositions can be in form of, e.g., a spray, a solution, a dispersion, a suspension, an emulsion, powders, gels including hydrogels, pastes, ointments, creams, drenches, delivery devices, suppositories, enemas, implants, aerosols, microcapsules, microspheres, nanoparticles, liposomes, dressings, bandages, plasters, tooth paste, dental care compositions, and in other suitable form. The bioadhesive compositions can be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988. Pharmaceutically acceptable excipients for use in bioadhesive compositions for use according to the invention can be, for example, inert diluents or fillers, such as sucrose, sorbitol, sugar, mannitol, microcrystalline cellulose, carboxymethylcellulose sodium, methylcellulose, hydroxypropyl methylcellulose, ethylcellulose, starches including potato starch, calcium carbonate, sodium chloride, lactose, calcium phosphate, calcium sulfate or sodium phosphate; and lubricating agents including glidants and antiadhesives, for example, magnesium stearate, zinc stearate, stearic acid, silicas, hydrogenated vegetable oils or talc. Other pharmaceutically acceptable excipients can be colorants, flavouring agents, plasticizers, humectants, buffering agents, solubilizing agents, release modulating agents, etc. For application to the rectal or vaginal mucosa suitable compositions for use according to the invention include suppositories (emulsion or suspension type), suspensions, solutions, enemas, and rectal gelatin capsules (solutions or suspensions). Appropriate pharmaceutically acceptable suppository bases include cocoa butter, esterified fatty acids, glycerinated gelatin, and various water-soluble or dispersible bases like polyethylene glycols and polyoxyethylene sorbitan fatty acid esters. Various additives like, e.g., enhancers or surfactants can be incorporated.

For application to the nasal mucosa, nasal sprays and aerosols for inhalation can be suitable compositions for use according to the invention. In a typically nasal formulation, the active ingredients can be dissolved or dispersed in a suitable vehicle. The pharmaceutically acceptable vehicles and excipients and optionally other pharmaceutically acceptable materials present in the composition such as diluents, enhancers, flavouring agents, preservatives etc. are all selected in accordance with conventional pharmaceutical practice in a manner understood by the persons skilled in the art of formulating Pharmaceuticals.

For application to the oral cavity, teeth, skin or nail, the compositions for use according to the invention can contain conventionally non-toxic pharmaceutically acceptable carriers and excipients including microspheres and liposomes. The formulations include creams, ointments, lotions, liniments, gels, hydrogels, suspensions, solutions sticks, sprays, pastes, dressings, bandages, plasters, tooth paste, dental care compositions, and the like. The pharmaceutically acceptable carriers or excipients can include emulsifying agents, stabilizing agents, antioxidants, buffering agents, preservatives, humectants, penetration enhancers, chelating agents, gel forming agents, ointment bases, perfumes and skin protective agents.

Examples of emulsifying agents can be naturally occurring gums, e.g., gum acacia or gum tragacanth, naturally occurring phosphatides, e.g., soybean lecithin and sorbitan monooleate derivatives. Examples of antioxidants can be butylated hydroxy anisole (BHA), ascorbic acid and derivatives thereof, a-tocopherol and derivatives thereof, vitamin E, salts of sulphur dioxide, cysteine, citric acid, ascorbyl palmitate, butylhydroxytoluene, complexing agents, chelating agents, sodium pyrosulfite, EDTA and gallic acid esters. Examples of preservatives can be parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, propyleneglycol (increases the solubility of preservatives) benzalconium chloride, benzylalcohol, chlorhexidine diacetate, chlorhexidine digluconate, chlorbutol, phenetanol, phenols (phenol, o-cresol, p-cresol, chlorocresol, tricresol), alkanols (chlorobutanol, phenetanol), sorbic acid, and mercuri-compounds like e.g., phenylmercurinitrate. Examples of humectants can be glycerin, propylene glycol, sorbitol and urea. Examples of suitable release modulating agents for use according to the invention can be glycerol, sesame oil, soybean oil, lecithin and cholesterol. Examples of penetration enhancers can be oleic acid, propylene glycol, DMSO, triethanolamine, N,N-dimethylacetamide, N,N-dimethylformamide, 2-pyrrolidone and derivatives thereof, -tetrahydrofuryl alcohol and Azone. Examples of chelating agents can be sodium EDTA, citric acid and phosphoric acid. Examples of other excipients for use in compositions for use according to the invention can be edible oils like almond oil, castor oil, cacao butter, coconut oil, corn oil, cottonseed oil, linseed oil, olive oil, palm oil, peanut oil, poppyseed oil, rapeseed oil, sesame oil, soybean oil, sunflower oil, and teaseed oil; and of polymers such as carmelose, sodium carmelose, hydroxypropylmethylcellulose, hydroxyethylcellulose, hydroxypropylcellulose, chitosane, pectin, xanthan gum, carrageenan, locust bean gum, acacia gum, gelatin, and alginates, and solvents such as, e.g., glycerol, ethanol, propylene glycol, polyethylene glycols such as PEG 200 and PEG 400, Pluronic, polysorbate, and ethylene glycol. Examples of ointment bases can be beeswax, paraffin, cetyl palmitate, vegetable oils, sorbitan esters of fatty acids (Span®), Carbopol®, polyethylene glycols, and condensation products between sorbitan esters of fatty acids and ethylene oxide, e.g., polyoxyethylene sorbitan monooleate (Tween®).

Pharmaceutically acceptable carriers can be determined in part by the particular composition being administered, as well as by the particular method used to administer the composition. Accordingly, there is a wide variety of suitable formulations of pharmaceutical compositions for administering a pharmaceutically active agent in a viscous liquid composition (see, e.g., *Remington's Pharmaceutical Sciences*, Mack Publishing Co., Easton, Pa. 18$^{th}$ ed., 1990, incorporated herein by reference). The pharmaceutical compositions are generally formulated as sterile, substantially isotonic and in full compliance with all Good Manufacturing Practice (GMP) regulations of the U.S. Food and Drug Administration.

Reference to "performance modifiers" means those materials that help to improve the stability and/or performance of lipid-based suspending vehicles. In some embodiments, such improvements include changing the properties of a two-component vehicle, that is already a stable solution of lipid in non-aqueous solvent, by altering the viscosity or other properties of a vehicle. Other aspects of the invention include improving the solubility of one component in the other, thus stabilizing the vehicle.

Performance modifiers that reduce stiff phases that are sometimes formed on contact of a amphiphilic-based suspending vehicle with aqueous medium include, but are not limited to, ethyl acetate, sesame oil, dioctyl sulfosuccinate, cholesterol, polysorbate 20, polysorbate 80, sodium dodecyl sulfate, fatty acids like oleic, stearic, linoleic, myristic, tocopheryl acetate, and vitamin E TPGS.

Performance modifiers that are cosolvents, that may act a dissolution rate enhancer, phase modifier, viscosity modifier or processing aid include but are not limited to ethanol, tocopherols, vegetable oils (sesame, cottonseed, safflower, coconut, soybean, olive), caprylic/capric triglycerides, ethyl acetate, benzyl alcohol, glycofurol, thenyl oleate, N,N dimethyl acetamide, polyoxaester liquid polymers, N-methylpyrrolidone, polysorbate 80, polysorbate 20, castor oil, isopropyl myristate, triacetin, polyethylene glycol, lauryl lactate, lauryl alcohol, and combinations thereof.

Performance modifiers in accordance with the present invention can be used, for example, to improve the stability and/or the flowability of lipid-based suspending vehicles. For example, the use of performance modifiers aids in softening formations made at exit ports upon contact by the suspending vehicle with aqueous media, for example, bodily fluids. Performance modifiers, such as co-solvents, can also speed-up preparation of suspending vehicles and suspensions due to increased solubility of the lipid in co-solvents relative to a non-aqueous solvent. Performance modifiers can also be useful for reducing viscosity variations over small composition variations.

Reference to "suspending vehicle" means that the pharmaceutically active agent is substantially insoluble therein. Materials that are substantially insoluble generally remain in their original physical form throughout the lifespan of a dosage form containing the suspension. For example, solid particulates would generally remain particles. If necessary, the suspending vehicle may have other materials dissolved in them.

Reference to "stiff gels" means the gels that form within a suspending vehicle or pharmaceutical suspension upon contact with an aqueous medium that may be pliable but are substantially hard enough that they would impede flow out of a dosage form.

Furthermore, relevant compositions and conditions to be fulfilled for the individual components in the compositions are claimed in the claims and described in the Examples.

Example 1

An exemplary embodiment of liquid viscous compositions comprising a therapeutic protein or drug is the protein ω-interferon (ω-IFN) in a liquid composition of 1,2-Dioleoy-sn-glycero-3-phosphatidylcholine (DOPC):N-methylpyrrolidone (NMP) (3:1 w/w) or in a liquid composition of DOPC: lauryl lactate (LL) (3:2 w/w). A summary of results demonstrates that: (1) Protein release occurs from the liquid viscous compositions into a sink of aqueous media; (2) Release rate of ω-IFN from a composition comprising lauryl lactate:DOPC vehicles demonstrates that release occurs at a therapeutically effective rate to confirm feasibility; (3) ω-IFN in anhydrous suspension is stable; (4) α-tocopherol in combination with DOPC or DMPC can further include compounds to modify the rheological properties of the vehicle itself.

The objectives of the study are to: (a) assess the preliminary stability of ω-interferon at 40° C. in vehicles composed of a lipid (1,2-Dioleoy-sn-glycero-3-phosphatidylcholine (DOPC)) and a solvent (lauryl lactate (LL) or N-methylpyrrolidone (NMP)), (b) investigate the release of ω-interferon from these vehicles into aqueous media, and (c) evaluate pump performance using lipid-based vehicles in a release rate study.

1.1 Plan of Study

TABLE 1

Characterization of Various materials

| Material | Test | Method |
|---|---|---|
| NMP | Peroxide Content | EP 2000 2.5.5 Method A or Oxis Method |
| Vehicles | Moisture Content | Karl Fischer |
| Protein Particles | Protein Content | RP-HPLC and SEC |

Preparation and Evaluation of Suspension

Control particles (1:2:1 Protein:Sucrose:Methionine with 25 mM citrate buffer) was used for the study. The particle loading was approximately 10%, which is equivalent to drug loading of 1.67%. This is consistent with a unit dose of 25 μg/day.

The suspension is prepared in a dry box under nitrogen. Suspension composition is presented in Table 2 and 3.

TABLE 2

| Composition of DOPC/NMP Formulation | |
|---|---|
| DOPC/NMP Formulation ID | PDP7-176-1, 3 |
| Particle Source | Spray-dried in Palo Alto facility |
| Vehicle Loading (3:1 DOPC:NMP) | 90% |
| Particle Loading | 10% |
| Protein Concentration | 1.67% |

TABLE 3

| Composition of DOPC/LL Formulation | |
|---|---|
| DOPC/LL Formulation ID | PDP7-176-2, 4 |
| Particle Source | Spray-dried in Palo Alto facility |
| Vehicle Loading (3:2 DOPC:LL) | 90% |
| Particle Loading | 10% |
| Protein Concentration | 1.67% |

Stability of the suspension was measured after storage at 40° C. under nitrogen in lyophilization vials. Stability samples was tested in triplicate at t=0, 2, and 4 weeks (5 mg ω-interferon per timepoint). Analysis was performed using RP-HPLC to determine purity with respect to oxidation and deamidation and using SEC to determine purity with respect to aggregation and precipitation.

A dissolution study was run with 6 mg formulation in 2 mL phosphate buffered saline (PBS) in Vacutainers®. These samples was incubated at 40° C. and tested at t=0, 1, 3, and 7 days.

Release rate formulations was prepared after results for t=0 stability and t=1 week dissolution samples are generated (assuming reasonable protein recoveries).

TABLE 4

| Tests and Observations to be made on the Dynamic Capillary Tube Samples in Exp. PDP7-176 | |
|---|---|
| Test to be Performed | Frequency and Details of Test |
| X-Ray to determine location of piston | Before immersing membrane in PBS buffer and approximately every two weeks thereafter |
| Quantify soluble and insoluble ω-interferon released from implant | Samples were collected approximately twice per week. Quantify protein with HPLC or other analytical method. Guanidine HCl used to redissolve insoluble protein. |
| Visual observations of glass capillary tubes | Approximately weekly once glass tubes are immersed in PBS. |
| Visual measurement of water ingress into glass capillary tubes | Weekly once glass tubes are immersed in PBS. |

Suspension Preparation

Suspensions for stability and dissolution testing was prepared at a target batch size of 2.0 grams. This batch size is determined by the quantity of protein particles required. Suspension is prepared in a dry box under nitrogen.

Lauryl Lactate/DOPC Vehicle and Suspension Preparation for Use in Release Rate, Stability, and Dissolution Testing 1. Preheat a hot plate to maintain a target surface temperature of 80° C.
2. Weigh 3.00 g DOPC
3. Weigh 2.00 g LL
4. Heat to 80° C. on hot plate and mix with stainless steel spatula by hand 5. Transfer 2.025 g of Vehicle and add 0.225 g of protein particles.
6. Using a stainless steel spatula, manually incorporate the protein particles into the vehicle. Continue to hand mix the suspension for 15 minutes while warming on the hot plate.
7. Fill suspension into syringe, de-aerate under vacuum, seal syringe and store refrigerated.

NMP/DOPC Vehicle and Suspension Preparation for Use in Release Rate Testing

1. Preheat a hot plate to maintain a target surface temperature of 80° C.
2. Weigh 3.75 g DOPC
3. Weigh 1.25 g NMP
4. Heat to 80° C. on hot plate and mix with stainless steel spatula by hand
5. Transfer 2.025 g of Vehicle and add 0.225 g of protein particles.
6. Using a stainless steel spatula, manually incorporate the protein particles into the vehicle. Continue to hand mix the suspension for 15 minutes while warming on the hot plate.
7. Fill suspension into syringe, de-aerate under vacuum, seal syringe and store refrigerated.

1.2 Particle Preparation

Protein-excipient solution was spray dried to result in spray-dried particles. Particle size can be from about 1 to about 10 μm in diameter. Other procedures for creating particles include, but are not limited to, lyophilization or supercritical fluid processing.

1.3 System Assembly

Systems were assembled by loading suspension of the liquid composition into a formulation compartment of the osmotic delivery device. A cap with an orifice was slowly screwed onto the shell of the osmotic delivery device. The exit orifice serves as a diffusion moderator for release of the liquid composition.

Example 2

Table 5 shows the solubility of a therapeutic protein, ω-interferon, in an non-aqueous liquid solvent. Thirteen non-aqueous liquid solvent candidates were identified to develop a solution formulation or a suspension formulation based on solubility of ω-interferon. The solvents at the top, e.g., lauryl lactate, are potential suspension solvents. The character of the solvents changes to potential solution solvents in combination with ω-interferon, e.g., glycerol formal, benzyl benzoate, DMSO, or glycerin.

Non-aqueous liquid solvents, such as glycerol formal, benzyl benzoate, DMSO, or glycerin are useful in combination with small molecule therapeutic drugs, therapeutic lipid prodrug, or therapeutic protein to form suspension formulations with drugs. Furthermore, non-aqueous liquid solvents, such as lauryl lactate, lauryl alcohol, NMP, ethanol, PEG 400, 1:1 benzyl benzoate:benzyl alcohol, benzyl alcohol, ethyl hexyl lactate are useful in combination with small molecule therapeutic drugs, therapeutic lipid prodrug, or therapeutic protein to form suspension formulations with drugs.

TABLE 5

ω-Interferon Solubility in Non-aqueous liquid solvents

| Solvent | Concentration by UV (mg/ml) | Concentration by rp-HPLC | Concentration by SEC (mg/ml) | Expected Conc (mg/ml) |
|---|---|---|---|---|
| Lauryl lactate | <0.1 | N/A | N/A | 10.00 |
| Lauryl alcohol | <0.1 | N/A | N/A | 10.00 |
| NMP | <0.1 | 0.00 | 0.00 | 25.00 |
| Ethanol | <0.1 | 0.00 | 0.00 | 25.00 |
| PEG 400 | <0.1 | 0.00 | 0.00 | 25.00 |
| 1:1 Benzyl benzoate:Benzyl alcohol | <0.1 | 0.00 | 0.00 | 10.00 |
| Benzyl alcohol | 0.14 | 0.00 | 0.00 | 10.00 |
| Ethyl hexyl lactate | 0.37 | 0.00 | 0.00 | 10.00 |

Example 3

FIG. 1 shows the shear rate effect on various DOPC vehicle formulations at 37° C. DOPC vehicle formulations that were tested include, DOPC/DMSO (3:1), DOPC/Gly (2.45:1), DOPC/NMP (2:1), DOPC/LL (2:1), DOPC/LA (2:1). The results demonstrate that at increasing shear rate DOPC formulations can be shear thinning. Shear thinning is an important property to facilitate the manufacturing process of the viscous liquid formulations.

Example 4

FIG. 2 shows the temperature effect on viscosity of DOPC formulations. The viscosity of various DOPC formulations was measured at various temperatures under a shear stress of 0.04 per second. The results indicate that viscosity of DOPC formulations is temperature dependent.

Example 5

FIG. 3 shows the shear rate effect on various PHSPC vehicle formulations at 37° C. PHSPC vehicle formulations that were tested include PHSPC/GF (1:1), PHSPC/LL (1:1), PHSPC/LA (2:1), PHSPC/GF (2.5:1). The results demonstrate that at increasing shear rate PHSPC formulations can be shear thinning. Shear thinning is an important property to facilitate the manufacturing process of the viscous liquid formulations.

Example 6

FIG. 4 shows the temperature effect on viscosity of PHSPC formulations. The viscosity of various PHSPC formulations was measured at various temperatures under a shear stress of 0.04 per second. The results indicate that viscosity of PHSPC formulations is temperature dependent.

Example 7

FIG. 5 displays images of DOPC formulations, e.g., DOPC/NMP (3:1), DOPC/LL (1:1), DOPC:$H_2O$ (1:9) visualized by polarized microscopy. All samples are birefringent, suggesting formation of lipid vesicles in the suspension.

Example 8

FIG. 6 displays images of PHSPC formulations, e.g., PHSPC/GF (1:1), PHSPC/LL (1:1), PHSPC:$H_2O$ (1:9), PHSPC/LA (2:1), as visualized by polarized microscopy. PHSPC/LL formulation is not birefringent suggesting dissolution of PHSPC in LL. However all other samples are birefringent, suggesting formation of lipid vesicles in the suspension.

Example 9

Table 6 summarizes the solubility and rheology of lipids in various solvents. Parameters measured were viscosity at 37° C. (in poise), shear thinning at 37° C. (sec$^{-1}$), temperature effect on viscosity (poise).

TABLE 6

Rheology and Solubility of Lipids in Non-aqueous liquid solvents

| Lipid | Solvent | Lipid:Solvent Ratio | | Viscosity at 37° C. (poise) | Shear Thinning at 37° C. (1/s) | Temp effect (° C.) | Viscosity (poise) | Comments |
|---|---|---|---|---|---|---|---|---|
| DOPC | BA | 1.35 | 1 | | | | | Low viscosity to the eye |
| DOPC | BA | 1.78 | 1 | | | | | Low viscosity to the eye |
| DOPC | NMP | 2 | 1 | 33000-170 | 0.04-10 | 5-47 | 114000-1380 | |
| DOPC | NMP | 2.8 | 1 | 12900 | 0.04 | 5-70 | 12600-8200 | No stress sweep data |
| DOPC | NMP | 3.5 | 1 | 19500 | 0.04 | 5-70 | 200000-9000 | No stress sweep data |
| DOPC | GF | 0.5 | 1 | | | | | Low viscosity to the eye |
| DOPC | GF | 1 | 1 | | | | | Low viscosity to the eye |
| DOPC | GF | 2.45 | 1 | 10 | No | No | | |
| DOPC | DMSO | 3 | 1 | 35000-700 | 0.04-2.5 | 5-70 | 5e4-5e3 | |
| DOPC | LL | 2 | 1 | 420000-7Q0QO | 0.04-0.25 | 5-70 | 2e6-4.5e4 | |
| DOPC | LA | 2 | 1 | 8760-870 | 0.04-1 | 10-35 | 3.7e5-4.8e4 | Gel crash above 35° C. |
| PHSPC | GF | 1 | 1 | 5220-440 | 0.04-1 | 5-70 | 5e3-9.5e−1 | |
| PHSPC | GF | 2.5 | 1 | 1300-700 | 0.04-1 | 10-70 | 2.25e4-2.8e2 | |
| PHSPC | LL | 1 | 1 | 13000-130 | 0.04-0.65 | 5-70 | 2e4-3 | |
| PHSPC | LA | 2 | 1 | 125 | No | 20-70 | 7e3-5 | |

Example 10

Table 7 summarizes moisture levels in lipid vehicles. The moisture level of the lipid, e.g., DOPC, HSPC, PHSPC, or DMPC, is measured after vacuum at room temperature for 48 hours. Lipid vehicles with lower moisture level can be included in viscous liquid compositions.

TABLE 7

Lipid Moisture Level

| Lipid | Avg. Moisture (%) |
|---|---|
| DOPC | 0.6 ± 0.2 |
| HSPC | 1.85 ± 0.64 |
| PHSPC | 1.02 ± 0.52 |
| DMPC | 0.6 |

Example 11

Figure 7:
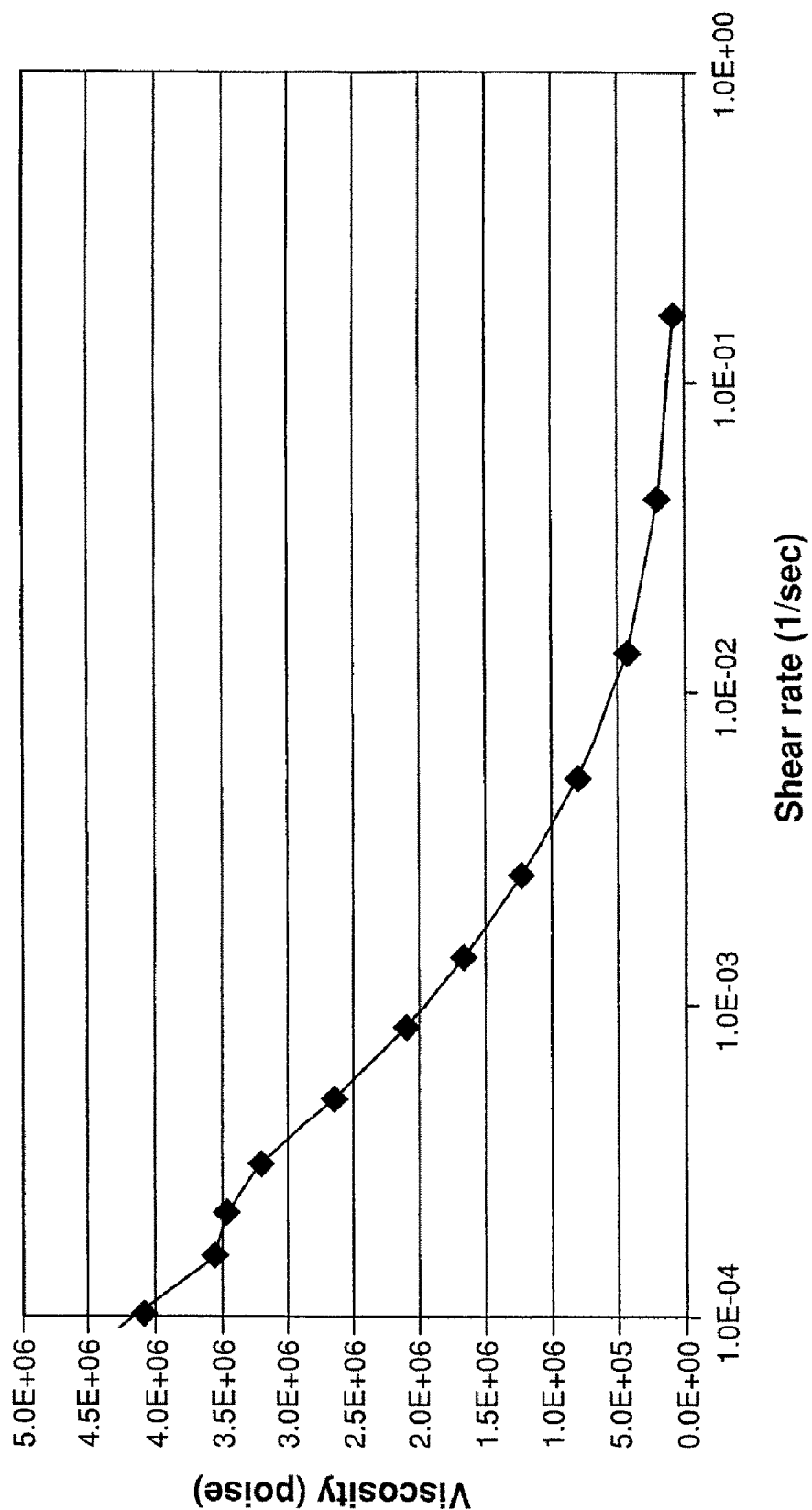
FIG. 7 shows a shear rate effect on a DOPC:LL vehicle formulation at 37° C.

FIG. 7 shows a shear rate effect on a DOPC:LL vehicle formulation at 37° C. The vehicle formulations tested was DOPC/LL (3:2). The results demonstrate that at increasing shear rate, the DOPC/LL formulation can be shear thinning. At 0.014 sec$^{-1}$, η=412,000 poise. At 0.16 sec$^{-1}$, η=60,600 poise. In a diffusion moderator, the shear rate, is approximately $10^{-4}$ to $10^{-2}$ sec$^{-1}$. In a mixer, the shear rate is approximately $10^1$ to $10^2$ sec$^{-1}$. The ratio of DOPC/LL can be adjusted to achieve an appropriate viscosity.

Example 12

Figure 8:
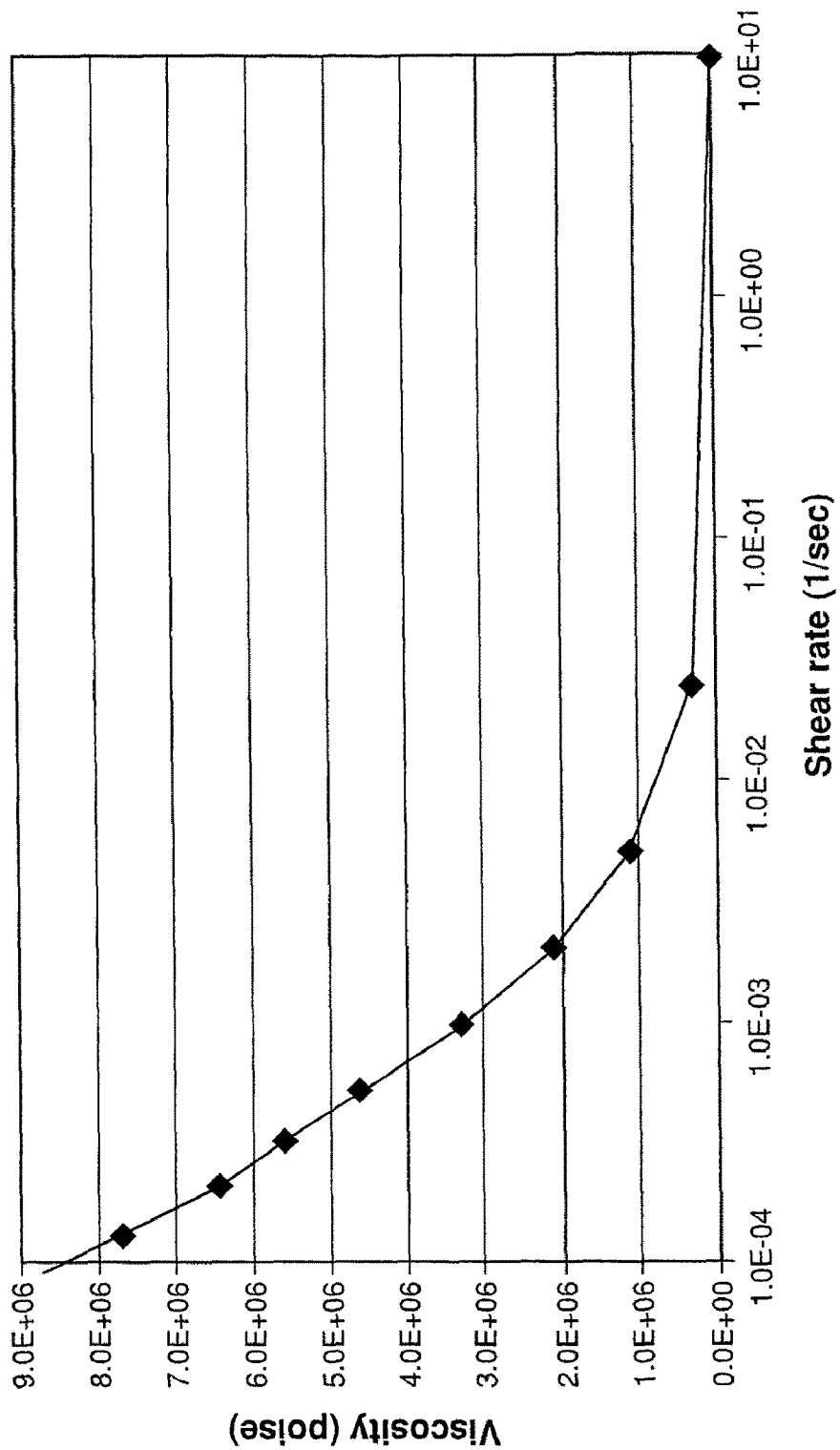
FIG. 8 shows a shear rate effect on a DOPC:NMP vehicle formulation at 37° C.

FIG. 8 shows a shear rate effect on a DOPC:NMP vehicle formulation at 37° C. The vehicle formulations tested was DOPC/NMP (3:1). The results demonstrate that at increasing shear rate, the DOPC/NMP formulation can be shear thinning. At 0.024 sec$^{-1}$, η=310,000 poise. At 9.7 sec$^{-1}$, η=1,040 poise. The ratio of DOPC/NMP can be adjusted to achieve an appropriate viscosity.

Example 13

Figure 9:
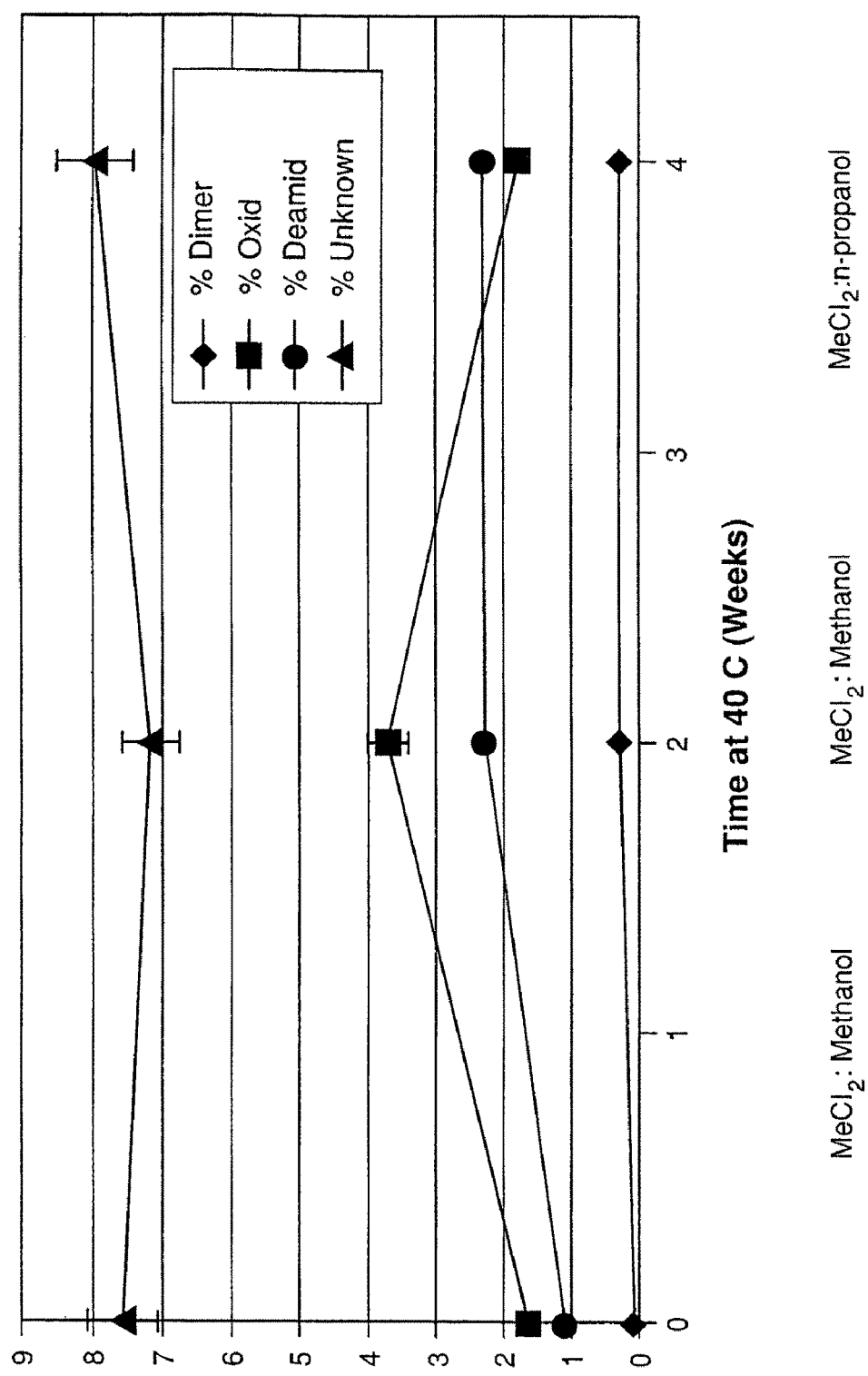
FIG. 9 shows the stability of ω-interferon in DOPC:LL suspension at 40° C.

FIG. 9 shows the stability of ω-interferon in DOPC:LL suspension at 40° C. The percentage of dimer, oxide and deamide of ω-interferon was measured at 0, 2, and 4 weeks for ω-interferon in DOPC:LL suspension by MeCl$_2$:Methanol (95:5) or MeCl$_2$:n-propanol (50:50) extraction. The DOPC:LL suspension particle at 0 weeks contained 1.63% oxide, 1.45% deamide, 7.94% unknown, and 0.07% dimer. ω-interferon in DOPC:LL suspension was stable for 4 weeks at 40° C.

Example 14

Table 8 shows ω-interferon recovery from viscous liquid suspensions, DOPC:NMP or DOPC:LL. Assessment of in vitro release rate recovery was measured after adding 6 mg of viscous liquid suspensions to 2 ml of release rate medium (phosphate-buffered 0.8% saline). Release of ω-IFN from the suspension into the medium was measured from t=0 days to t=7 days. Percent recovery is based on a protein concentration of 1.67 wt % in the viscous liquid suspension formulation. The results indicate that greater than 90% soluble ω-IFN is recovered after incubation for seven days at 37° C.

TABLE 8

ω-Interferon Recovery from Viscous Liquid Suspension

| Time (days) | % Recovery NMP:DOPC | % Recovery LL:DOPC |
|---|---|---|
| 0 | 88.96 (5.56) | Not available |
| 7 | 95.09 (5.3) | 91.16 (0.45) |

% Recovery data is an average of 3 samples (±SD).

Example 15

In the study in Example 14 (Table 8), the DOPC:NMP viscous liquid suspension showed a slight increase in recovery of soluble ω-interferon from t=0 days to 7 days. A further experiment was performed to determine whether a delay in release of protein to release rate medium was due to the fact that viscous liquid suspensions do not dissolve or disperse in phosphate-buffered saline (PBS). To compare release rates, ω-interferon concentration was measured in aqueous solution. n-propanol was added to dissolve lipid, and ω-interferon was measured again to determine whether addition of non-aqueous liquid solvent result in higher protein recoveries.

Figure 10:
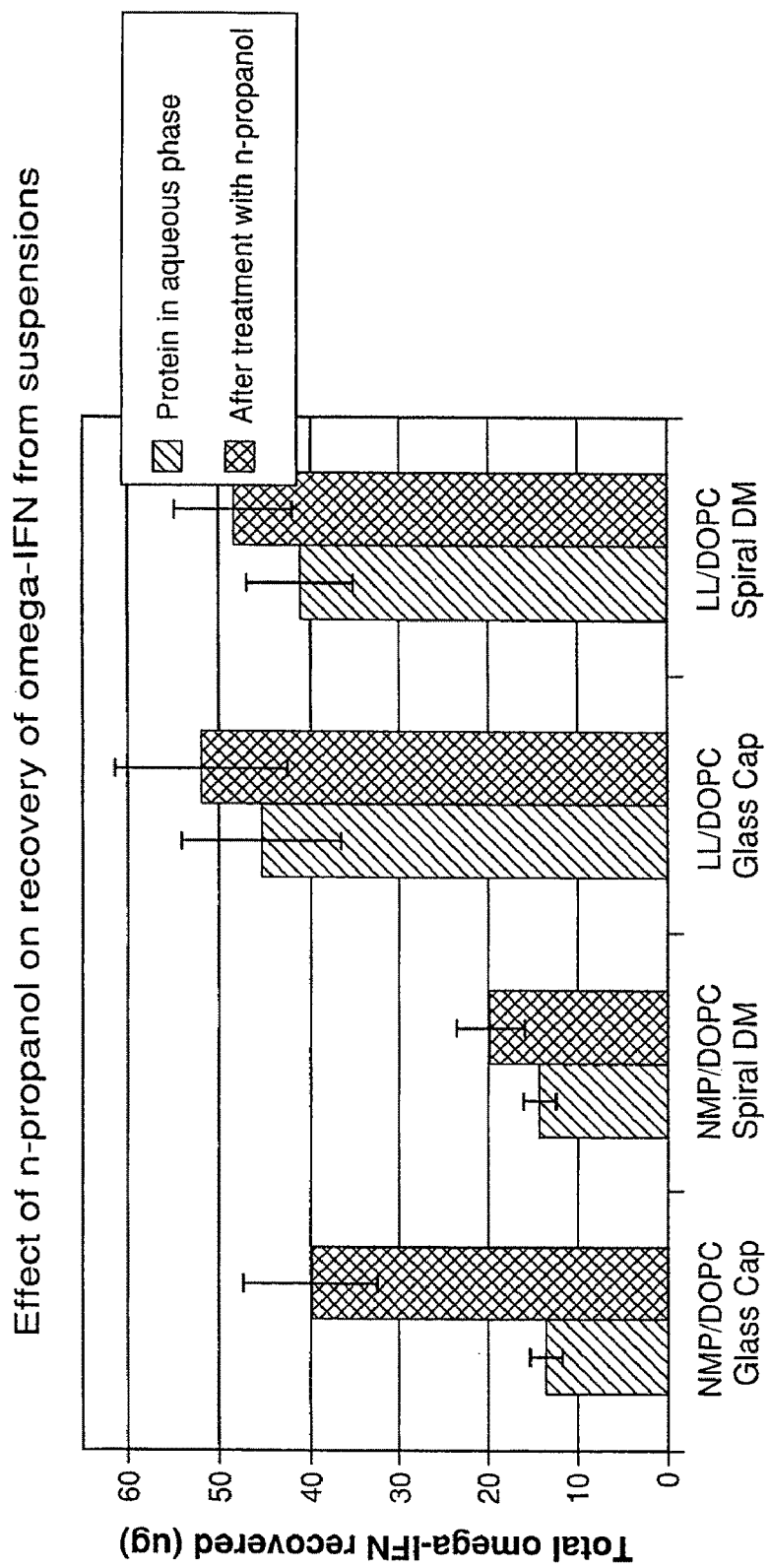
FIG. 10 shows the effect of n-propanol on recovery of ω-interferon from DOPC:NMP or DOPC:LL suspensions.

FIG. 10 shows the effect of n-propanol on recovery of ω-interferon from DOPC:NMP or DOPC:LL suspensions. The results show an increase in total ω-IFN recovered into an aqueous phase from DOPC:NMP or DOPC:LL suspensions following treatment with N-propanol. Increased recovery following N-propanol treatment occurred in both delivery systems, glass cap and spiral DM.

Example 16

Figure 11:
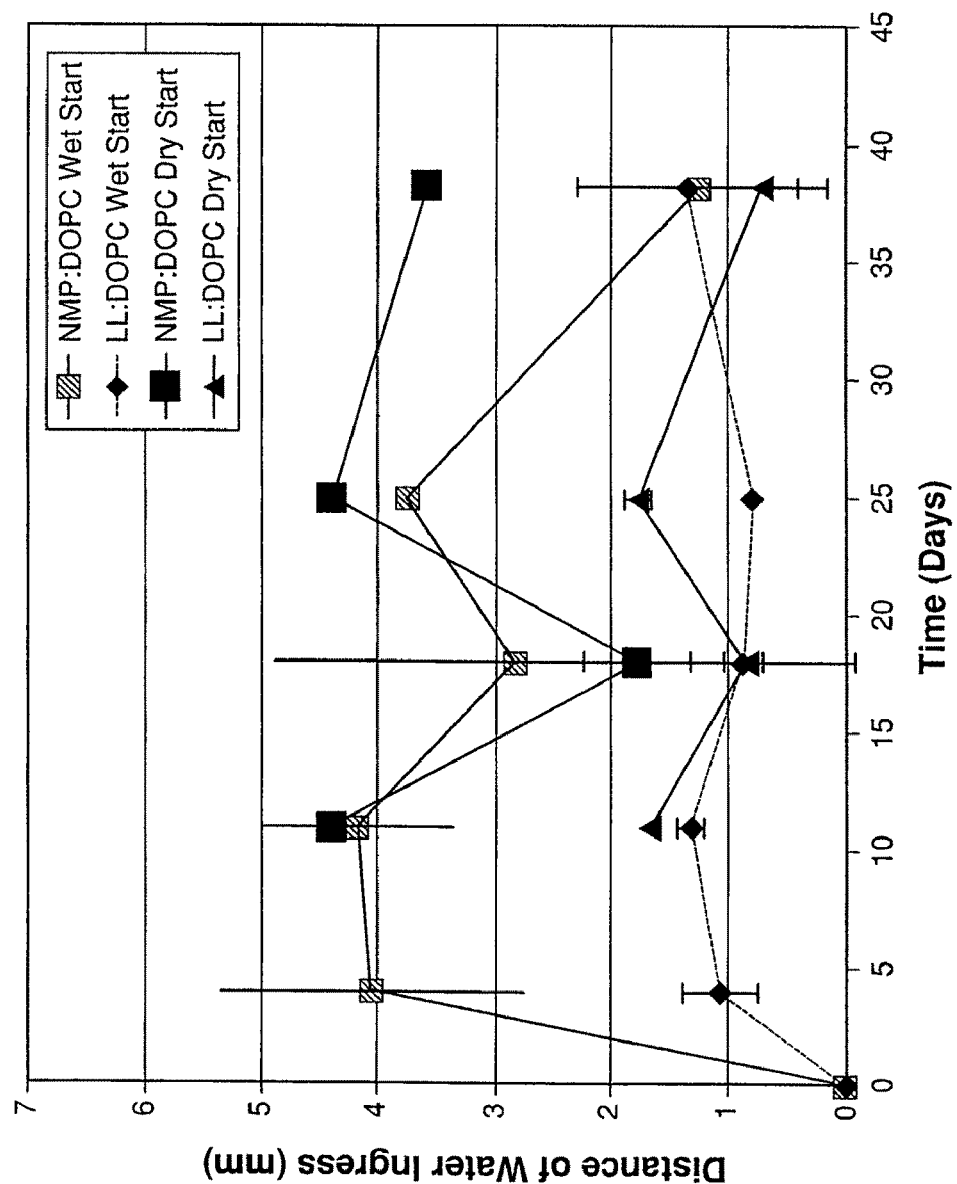
FIG. 11 shows water ingress into model diffusion moderators for viscous liquid formulations, DOPC:LL or DOPC:NMP.

Water ingress into model diffusion moderators was measured for viscous liquid formulations, DOPC:LL or DOPC:NMP. See FIG. 11. Measured after 38 days, the distance of water ingress into capillary tubes of diffusion moderators was less than 5 mm for viscous liquid formulations, DOPC:LL or DOPC:NMP. Less water ingress was observed with the DOPC:LL formulation than with the DOPC:NMP formulation. Minimal water ingress into the device, as shown in FIG. 11, has been shown to be advantageous to protein delivery from the DUROS® osmotic delivery device.

Example 17

Additional solvents in combination with a lipid, e.g., DOPC, are useful in suspension formulations of viscous liquid compositions for parenteral drug delivery. Solvents that are useful in a viscous liquid formulation have hydrophobic character, for example, sesame oil, vitamin E (α-tocopherol), or silicon medical fluid (SMF, polydimethylsiloxane).

Example 18

Figure 12:
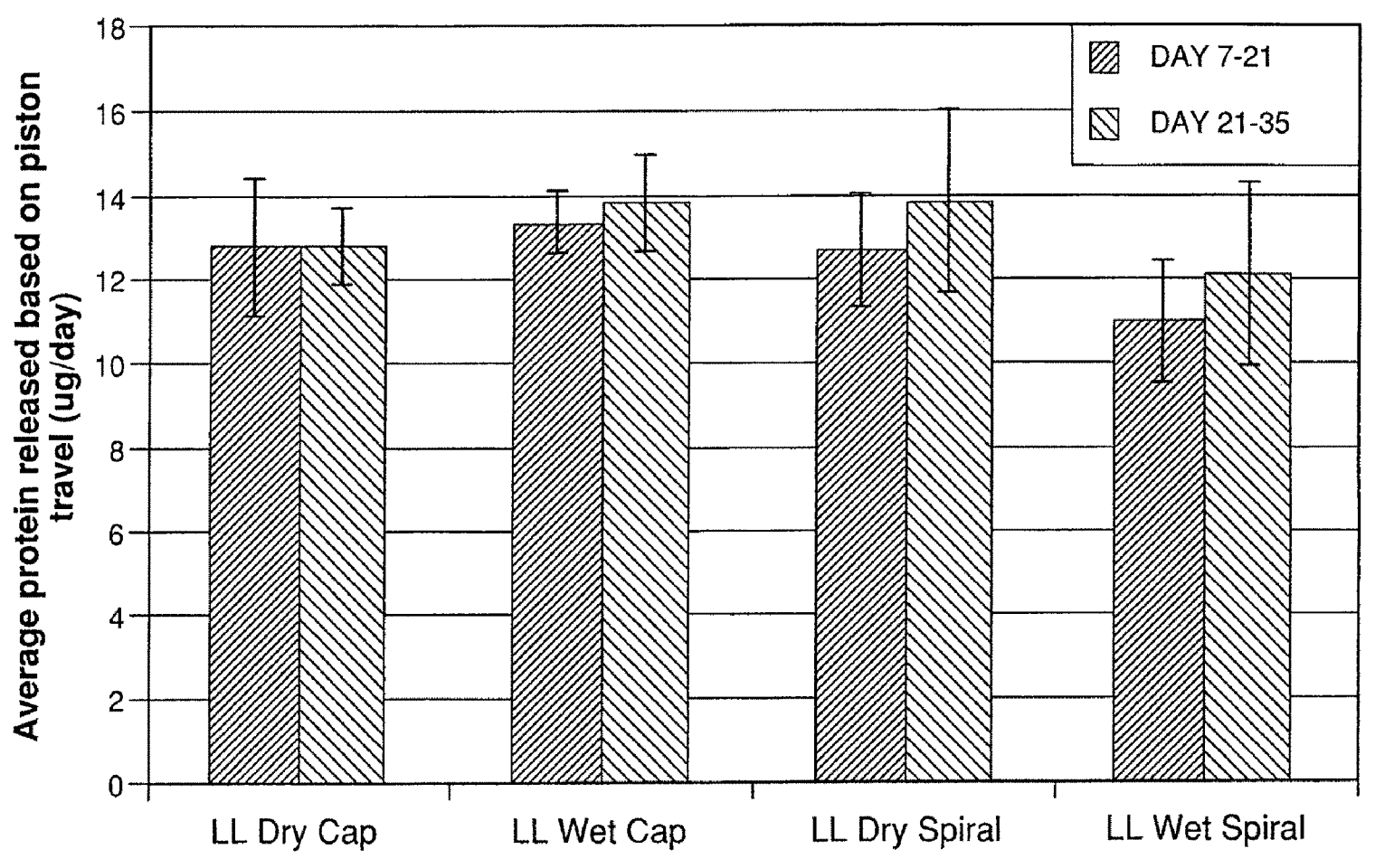

FIG. 12 shows a measure of average protein released from a delivery device based upon piston movement within the device. Based on piston movement, delivery of the DOPC:LL viscous liquid formulation is at target. Volumetric flow rate is consistent for the periods between Day 7 to 21 and Day 21 to 35. Target flow rate is 1.5 μl per day. Density of the viscous liquid formulation is assumed to be approximately 1 gm/ml.

Example 19

Figure 13:
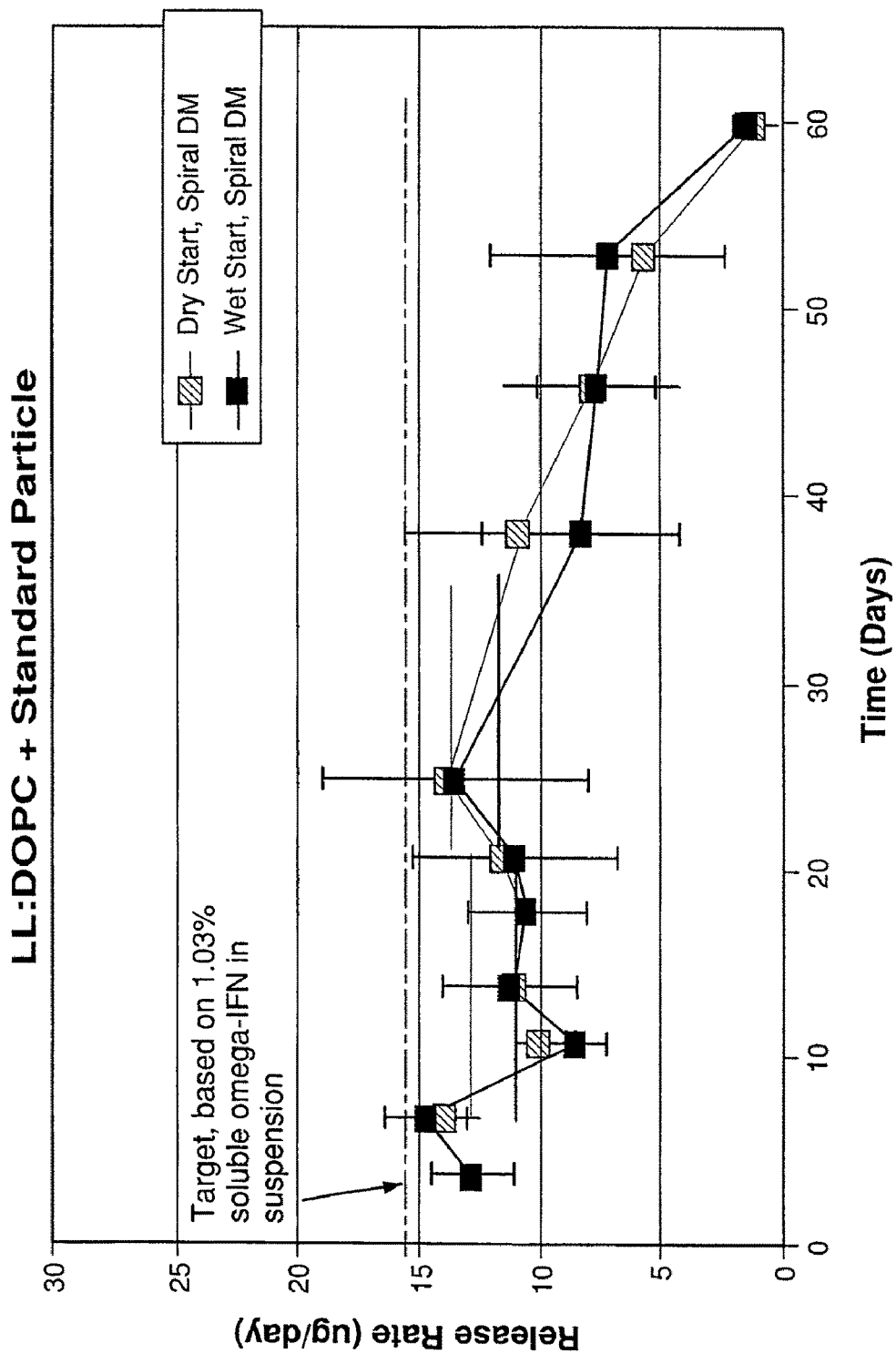
FIG. 13 shows piston movement in a delivery device correlates to the average protein released from the device.

FIG. 13 shows that piston movement in a delivery device correlates to the average protein released from the device. Release of soluble ω-interferon from DOPC:LL (3:2) formulations is closer to target when target is adjusted based on x-ray results of the delivery device. Release rate samples were treated with n-propanol. The target is based on 1.03% soluble ω-interferon in suspension.

Example 20

ω-interferon is stable in DOPC:sesame oil (1.5:1) viscous liquid composition for up to four weeks at 40° C. See Table 9. Percent oxidation shows an increase from t=0 weeks to t=4 weeks. Consistency and viscosity of the viscous liquid composition indicates that sesame oil can be added as a co-solvent with vitamin E (α-tocopherol) in combination with a lipid, e.g., DOPC.

TABLE 9

Stability of ω-interferon in DOPC: sesame oil viscous liquid compositions

|  | % Monomer | % Dimer | % Oxidation | % Deamidation | % Unknown |
|---|---|---|---|---|---|
| Spray dried Particle | 99.67 (0.01) | 0.23 (0.01) | 1.9 (0.39) | 2.02 (0.01) | 7.17 (0.44) |
| t = 0 SesOil:DOPC | 99.87 (0.03) | 0.14 (0.03) | 2.1 (0.17) | 1.27 (0.37) | 8.72 (0.82) |
| t = 2 wks SesOil:DOPC | 99.67 (0.02) | 0.02 (0.01) | 3.78 (0.03) | 1.56 (0.04) | 7.57 (0.56) |
| t = 4 wks SesOil:DOPC | 99.85 (0.00) | 0.14 (0.01) | 4.29 (0.13) | 2.55 (0.10) | 5.59 (0.24) |

Data is an average of four samples (±SD).

Example 21

DOPC has been combined with various solvents (1:1 weight ratio) to yield a viscous liquid composition as shown in Table 10. Lipid and solvent are mixed and heated between approximately 65 to 100° C. with continued mixing. Suitability of various solvents in the composition was evaluated.

TABLE 10

Analysis of properties of various solvent in combination with lipid, DOPC

| Solvent | Result | Action |
|---|---|---|
| Vitamin E (α-tocopherol) | Produces clear gel. | Pursue |
| Ethyl oleate | Clear, low viscosity gel. | Pursue |
| Caprylic capric triglyceride | Clear, low viscosity gel. | Pursue |
| Vegetable oils (sesame, soy, cottonseed oil) | With DOPC, physical separation seen over time. | |
| Poly oxyl 35 castor oil (PEG 35 Castor Oil) | With DOPC, physical separation seen over time. | |
| Silicone medical fluid (SMF) | DOPC not soluble in solvent. | |
| Poly ethylene glycol 400 (PEG) | DOPC not soluble in solvent. | |
| Polysorbate 20, 80 | DOPC not soluble in solvent. | |

Example 22

Figure 14:
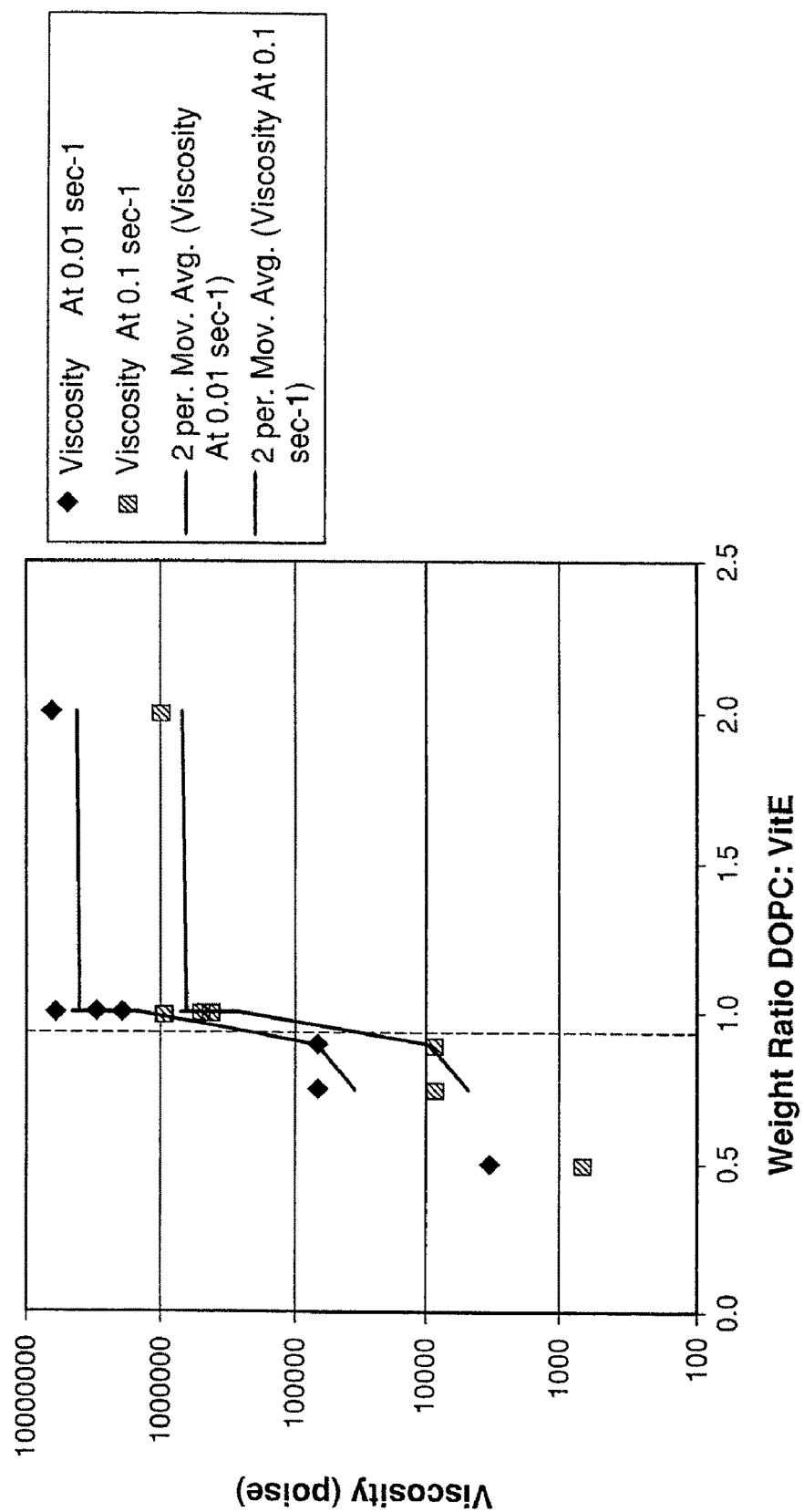
FIG. 14 shows viscosities of various DOPC:VitE formulations at various weight ratios.

Suspending vehicles comprising DOPC and Vitamin E were prepared at various weight ratios and viscosity was measured. FIG. 14 shows that viscosity increases by two orders of magnitude with a 5% change in composition. At a ratio of 0.75:1 DOPC:VitE, samples looked thin to the eye in that they flowed fairly easily when the sample vial was tipped on its side. At a ratio of 0.9:1, samples looked thicker than 0.75:1, and there was still flow when the sample vial was tipped on its side.

Example 23

A performance modifier is added to suspending vehicles of Example 22. It is desirable to reduce large variation of viscosity due to small variations in composition. A viscosity change of less than a factor of 10 is obtained over a composition change of 10% DOPC by weight.

Example 24

Suspending vehicles comprising DOPC and Vitamin E were prepared at various weight ratios and were exposed to aqueous media. In some examples, PBS was used as an aqueous medium. In other examples, Bovine Serum (adult) Sigma product B2771, lot 29H8401 was used. Samples were observed at room temperature at various times from 0 to 24 hours from the time that the aqueous media was added to the suspending vehicle. Table 11 shows that stiff phases, for example, gels, are produced upon contact of the suspending vehicles with aqueous media. Such formation of stiff phases could lead to plugging of a diffusion moderator of a dosage form, such as a DUROS device.

TABLE 11

Analysis of properties of various suspending vehicles without a performance modifier upon contact with aqueous media

| Sample (Weight ratios) | Aqueous Media Added (% by weight) | Result: Physical properties of resulting phase |
|---|---|---|
| DOPC:VitE 0.75:1 | 10% PBS | stiff but pliable |
| DOPC:VitE 0.75:1 | 25% PBS | stiff but pliable, excess water |
| DOPC:VitE 0.75:1 | 50% PBS | stiff but pliable, excess water |
| DOPC:VitE 1:1 | 10% PBS | stiff but pliable |
| DOPC:VitE 1:1 | 25% PBS | stiff but pliable, excess water |
| DOPC:VitE 1:1 | 50% PBS | stiff but pliable, excess water |
| DOPC:VitE 0.75:1 | 10% serum | Stiff, pliable, but more crumbly than when PBS is added, excess aqueous phase |
| DOPC:VitE 0.75:1 | 25% serum | Stiff, pliable, but more crumbly than when PBS is added, excess aqueous phase |
| DOPC:VitE 0.75:1 | 50% serum | Stiff, pliable, but more crumbly than when PBS is added, excess aqueous phase |

Example 25

Suspending vehicles comprising DOPC, Vitamin E, and a performance modifier were prepared. In some examples, the performance modifier was sesame oil. In one example, the performance modifier was ethyl acetate. PBS was used as an aqueous medium. Samples were observed at room temperature at various times from 0 to 24 hours from the time that the aqueous media was added to the suspending vehicle. Table 12 shows that unlike the suspending vehicles prepared without either sesame oil or ethyl acetate, soft phases are produced upon contact of the suspending vehicles with aqueous media. As such, the addition of sesame oil or ethyl acetate will soften gels or the like that result from the addition of aqueous media to suspending vehicles that do not contain a performance modifier.

TABLE 12

Analysis of properties of various suspending vehicles having a performance modifier upon contact with aqueous media

| Sample (Weight ratios) | Aqueous Media Added (% by weight) | Result: Physical properties of resulting phase |
|---|---|---|
| DOPC:VitE 0.75:1 | 25% PBS, then added 10% ethyl acetate | softer |
| DOPC:solvent 1.5:1 (Solvent = 75:25 VitE:SesOil) | 25% PBS | soft phase, very easy to move in vial |
| DOPC:solvent 1.5:1 (Solvent = 75:25 VitE:SesOil) | 50% PBS | soft phase, very easy to move in vial |

Example 26

A suspending vehicle comprising DOPC and Vitamin E was prepared without a performance modifier according to the following.

Weighed appropriate amount of DOPC in a glass jar. Weighed appropriate amount of Vitamin E directly onto the DOPC. Allowed mixture to incubate in 90° C. oven for 10 minutes. Transferred to Keyence Hybrid mixer. A hybrid mixer operates by applying a large, continuous, centrifugal force, produced by combination of the rotation of the material container and the revolution in a certain radius, removing air bubbles from the material while blending its contents. Mixed for 20 minutes in Keyence mixer. Incubated at 37° C. overnight. Heated on 85° C. hotplate for 10 minutes.

Mixed by hand with spatula for 5 minutes. Incubated sample in 90° C. oven for 10 minutes. Transferred to Keyence Hybrid mixer. Mixed for 20 minutes in Keyence mixer. Heated on 85° C. hotplate for 10 minutes.

Mixed by hand with spatula for 10 minutes. Incubated sample in 90° C. oven for 10 minutes. Transferred to Keyence Hybrid mixer. Mixed for 20 minutes in Keyence mixer. Incubated at 37° C. overnight. Heated on 85° C. hotplate for 15 minutes.

Mixed by hand with spatula for 10 minutes. Transferred to Keyence Hybrid mixer. Mixed for 20 minutes in Keyence mixer.

Total processing time took ~3 days to obtain a suspending vehicle that had DOPC substantially dissolved in Vitamin E.

Example 27

A suspending vehicle comprising DOPC and Vitamin E was prepared with a performance modifier, for example, ethanol, according to the following.

Weighed equal parts ethanol and DOPC into a test tube. Vortexed mixture for one minute on highest setting. Allowed mixture to sit for 5 minutes at room temperature. Weighed appropriate amount of Vitamin E into same test tube. Heated to 100-120° C. while mixing with a spring mixing blade for 1.5-3 hr under full vacuum. A spring mixing blade is essentially a spring attached to a straight rod.

Total processing time took ~4 hours to obtain a suspending vehicle that had DOPC substantially dissolved in a combination of ethanol and Vitamin E.

Example 28

A pharmaceutical suspension comprising DOPC, Vitamin E, sesame oil, and ω-interferon is prepared. The suspension is subjected to stability testing. It is desirable to obtain pharmaceutical suspensions that are shelf-stable for extended periods of time. The pharmaceutical suspension remains a homogeneous formulation for at least 3 months at 37° C. Visual observations of suspension appearance and measurement of drug levels throughout the suspension are used to determine that the suspension is homogenous.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the embodiments of the invention and that such changes and modifications can be made without departing from the spirit of the invention. It is, therefore, intended that the appended claims cover all such equivalent variations as fall within the true spirit and scope of the invention.

What is claimed:

1. A pharmaceutical composition comprising:
a particle formulation comprising a protein or peptide, sucrose, methionine, and citrate buffer, and
a suspending vehicle comprising a solvent selected from the group consisting of benzyl benzoate, lauryl lactate, and lauryl alcohol, wherein the particle formulation is dispersed in the suspending vehicle.

2. The pharmaceutical composition of claim 1, wherein said protein or peptide is selected from the group consisting of erythropoietin, human growth hormone, granulocyte macrophage colony stimulating factor, human growth hormone releasing hormone, insulin, infliximab, and glucagon-like peptide-1.

3. The pharmaceutical composition of claim 2, wherein the protein or peptide is glucagon-like peptide-1.

4. The pharmaceutical composition of claim 1, wherein the particle formulation comprises the protein or peptide, sucrose, methionine, and citrate buffer in a weight ratio of 1:2:1:2.15.

5. The pharmaceutical composition of claim 4, wherein the solvent is benzyl benzoate.

6. The pharmaceutical composition of claim 1, wherein the solvent is benzyl benzoate.

7. The pharmaceutical composition of claim 1, wherein the solvent is lauryl lactate.

8. The pharmaceutical composition of claim 1, wherein the suspending vehicle further comprises a lipid.

9. The pharmaceutical composition of claim 8, wherein the lipid is selected from the group consisting of dioleoyl phosphatidylcholine, dimyristoylphosphatidylcholine, dipalmitoylphosphatidylcholine, distearoylphosphatidylcholine, egg phosphatidylcholine, soy phosphatidylcholine, partially hydrogenated phosphatidylcholines, fully hydrogenated phosphatidylcholines, palmitoyl-oleoyl phosphatidylcholine, stearyloleoylphosphatidylcholine, dioleoy phosphatidylglycerol, dimyristoylphosphatidylglycerol, dipalmitoylphosphatidylglycerol, distearoylphosphatidylglycerol, and mixtures thereof.

10. The pharmaceutical composition of claim 1, wherein the particle formulation comprises spray-dried particles.

11. The pharmaceutical composition of claim 10, wherein the particle size is from about 1 μm to about 10 μm in diameter.

12. An osmotic drug delivery device comprising
a pharmaceutical composition comprising, (i) a particle formulation comprising a protein or peptide, sucrose, methionine, and citrate buffer, and (ii) a suspending vehicle comprising a solvent selected from the group consisting of benzyl benzoate, lauryl lactate, and lauryl alcohol, wherein the particle formulation is dispersed in the suspending vehicle.

13. The osmotic drug delivery device of claim 12, wherein said protein or peptide is selected from the group consisting of erythropoietin, human growth hormone, granulocyte macrophage colony stimulating factor, human growth hormone releasing hormone, insulin, infliximab, and glucagon-like peptide-1.

14. The osmotic drug delivery device of claim 13, wherein the protein or peptide is glucagon-like peptide-1.

15. The osmotic drug delivery device of claim 12, wherein the particle formulation comprises the protein or peptide, sucrose, methionine, and citrate buffer in a weight ratio of 1:2:1:2.15.

16. The osmotic drug delivery device of claim 15, wherein the solvent is benzyl benzoate.

17. The osmotic drug delivery device of claim 12, wherein the solvent is benzyl benzoate.

18. The osmotic drug delivery device of claim 12, wherein the solvent is lauryl lactate.

19. The osmotic drug delivery device of claim 12, wherein the suspending vehicle further comprises a lipid.

20. The osmotic drug delivery device of claim 19, wherein the lipid is selected from the group consisting of dioleoyl phosphatidylcholine, dimyristoylphosphatidylcholine, dipalmitoylphosphatidylcholine, distearoylphosphatidylcholine, egg phosphatidylcholine, soy phosphatidylcholine, partially hydrogenated phosphatidylcholines, fully hydrogenated phosphatidylcholines, palmitoyl-oleoyl phosphatidylcholine, stearyloleoylphosphatidylcholine, dioleoy phosphatidylglycerol, dimyristoylphosphatidylglycerol, dipalmitoylphosphatidylglycerol, distearoylphosphatidylglycerol, and mixtures thereof.

21. The osmotic drug delivery device of claim 12, wherein the particle formulation comprises spray-dried particles.

22. The osmotic drug delivery device of claim 21, wherein the particle size is from about 1 μm to about 10 μm in diameter.

* * * * *